US009220596B2

(12) United States Patent
Cook et al.

(10) Patent No.: US 9,220,596 B2
(45) Date of Patent: *Dec. 29, 2015

(54) BONE GRAFT MATERIALS AND METHODS

(71) Applicant: Biostructures, LLC, Newport Beach, CA (US)

(72) Inventors: Russell L. Cook, Newport Beach, CA (US); Duraid S. Antone, Aliso Viejo, CA (US)

(73) Assignee: Biostructures, LLC, Newport Beach, CA (US)

( * ) Notice: Subject to any disclaimer, the term of this patent is extended or adjusted under 35 U.S.C. 154(b) by 183 days.

This patent is subject to a terminal disclaimer.

(21) Appl. No.: 14/047,677

(22) Filed: Oct. 7, 2013

(65) Prior Publication Data

US 2014/0031950 A1    Jan. 30, 2014

Related U.S. Application Data

(63) Continuation of application No. 12/977,191, filed on Dec. 23, 2010, now Pat. No. 8,551,525.

(51) Int. Cl.
*A61L 27/10* (2006.01)
*A61L 27/24* (2006.01)
*A61L 27/12* (2006.01)
*A61F 2/28* (2006.01)
*A61L 27/46* (2006.01)
*A61K 38/00* (2006.01)

(52) U.S. Cl.
CPC . *A61F 2/28* (2013.01); *A61L 27/46* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | |
|---|---|---|
| 2,920,971 A | 1/1960 | Stookey |
| 3,090,094 A | 5/1963 | Schwartzwalder at al. |
| 3,679,360 A | 7/1972 | Grossman |
| 3,732,087 A | 5/1973 | Grossman |
| 3,833,386 A | 9/1974 | Wood et al. |
| 3,877,973 A | 4/1975 | Ravault |
| 3,907,579 A | 9/1975 | Ravault |
| 3,981,736 A | 9/1976 | Broemer et al. |
| 4,004,933 A | 1/1977 | Ravault |
| 4,149,893 A | 4/1979 | Aoki et al. |
| 4,273,131 A | 6/1981 | Olsen |
| 4,328,034 A | 5/1982 | Ferguson |
| 4,491,517 A | 1/1985 | Janovac |
| 4,609,923 A | 9/1986 | Boan et al. |
| 4,612,053 A | 9/1986 | Brown et al. |
| 4,619,655 A | 10/1986 | Hanker et al. |
| 4,643,982 A | 2/1987 | Kasuga et al. |
| 4,648,124 A | 3/1987 | Mantovani et al. |
| 4,652,534 A | 3/1987 | Kasuga |
| 4,673,355 A | 6/1987 | Farris et al. |
| 4,775,646 A | 10/1988 | Hench et al. |
| 4,789,663 A | 12/1988 | Wallace et al. |
| 4,791,939 A | 12/1988 | Maillard |
| 4,795,467 A | 1/1989 | Piez et al. |
| 4,812,854 A | 3/1989 | Boan et al. |
| 4,849,193 A | 7/1989 | Palmer et al. |
| 4,859,383 A | 8/1989 | Dillon |
| 4,868,580 A | 9/1989 | Wade |
| 4,880,610 A | 11/1989 | Constantz |
| 4,888,366 A | 12/1989 | Chu et al. |
| 4,897,250 A | 1/1990 | Sumita |
| 4,970,298 A | 11/1990 | Silver et al. |
| 4,983,573 A | 1/1991 | Bolt et al. |
| 5,001,169 A | 3/1991 | Nathan et al. |
| 5,034,352 A | 7/1991 | Vit et al. |
| 5,047,031 A | 9/1991 | Constantz |
| 5,084,050 A | 1/1992 | Draenert |
| 5,124,316 A | 6/1992 | Antoniades et al. |
| 5,129,905 A | 7/1992 | Constantz |
| 5,219,829 A | 6/1993 | Bauer et al. |
| 5,221,558 A | 6/1993 | Sonuparlak et al. |
| 5,236,458 A | 8/1993 | Ducheyne et al. |

(Continued)

FOREIGN PATENT DOCUMENTS

EP        0309241 B1    12/1993
WO    WO 2006/031196    3/2006

OTHER PUBLICATIONS

B. Marelli et al., "Three-Dimensional Mineralization of Dense Nanofibrillar Collagen-Bioglass Hybrid Scaffolds", Biomacromolecules, vol. 11, No. 6, Jun. 2010, pp. 1470-1479

B. Marelli et al., "Bulk Biomineralization of Dense Fibrillar Collagen-Bioglass Hybrid Scaffolds," (abstract) [retrieved on Sep. 23, 2010]. Retrieved from the Internet: http://www.biomaterials.org/abstracts/data/papers/2010/709.pdf.

Chen, X. et al., "A Biomimetic Material with a High Bio-responsibility for Bone Reconstruction and Tissue Engineering", Journal of Biomaterials Science, vol. 22, 2011, pp. 153-163.

(Continued)

*Primary Examiner* — Anand Desai
*Assistant Examiner* — Samuel Liu
(74) *Attorney, Agent, or Firm* — Cooley LLP

(57) ABSTRACT

Compositions, materials, methods and kits for bone grafting are described. In some embodiments, a bone graft composition includes about 15% to about 20% by weight collagen, about 55% to about 70% by weight bioactive glass, and about 15% to about 30% by weight a calcium phosphate. The bioactive glass and the calcium phosphate together are about 80% to about 85% by weight of the bone graft composition. In some embodiments, a bone graft composition includes a collagen matrix and a plurality of bioactive glass particulates dispersed throughout the collagen matrix. The collagen matrix is about 20% to about 60% by weight of the bone graft composition, and the bioactive glass is about 40% to about 80% of the bone graft composition. In some embodiments, a majority of the bioactive glass particulates are about 53 µm to about 425 µm in size.

17 Claims, 17 Drawing Sheets

(56) References Cited

U.S. PATENT DOCUMENTS

| | | |
|---|---|---|
| 5,236,786 A | 8/1993 | Newkirk et al. |
| 5,238,491 A | 8/1993 | Sugihara et al. |
| 5,256,292 A | 10/1993 | Cagle |
| 5,264,214 A | 11/1993 | Rhee et al. |
| 5,275,601 A | 1/1994 | Gogolewski et al. |
| 5,276,068 A | 1/1994 | Waknine |
| 5,281,265 A | 1/1994 | Liu |
| 5,290,289 A | 3/1994 | Sanders et al. |
| 5,292,678 A | 3/1994 | Dhong et al. |
| 5,294,395 A | 3/1994 | Broyer |
| 5,296,261 A | 3/1994 | Bouet et al. |
| 5,298,205 A | 3/1994 | Hayes et al. |
| 5,304,595 A | 4/1994 | Rhee et al. |
| 5,306,303 A | 4/1994 | Lynch |
| 5,306,500 A | 4/1994 | Rhee et al. |
| 5,322,675 A | 6/1994 | Hakamatsuka et al. |
| 5,328,955 A | 7/1994 | Rhee et al. |
| 5,336,642 A | 8/1994 | Wolcott |
| 5,338,334 A | 8/1994 | Zhen et al. |
| 5,338,356 A | 8/1994 | Hirano et al. |
| 5,383,931 A | 1/1995 | Hehli et al. |
| 5,383,932 A | 1/1995 | Wilson et al. |
| 5,409,982 A | 4/1995 | Imura et al. |
| 5,425,770 A | 6/1995 | Piez et al. |
| 5,427,754 A | 6/1995 | Nagata et al. |
| 5,458,653 A | 10/1995 | Davidson |
| 5,470,803 A | 11/1995 | Bonfield et al. |
| 5,494,677 A | 2/1996 | Giampapa |
| 5,496,399 A | 3/1996 | Ison et al. |
| 5,522,893 A | 6/1996 | Chow et al. |
| 5,525,148 A | 6/1996 | Chow et al. |
| 5,531,791 A | 7/1996 | Wolfinbarger, Jr. |
| 5,543,441 A | 8/1996 | Rhee et al. |
| 5,545,226 A | 8/1996 | Wingo et al. |
| 5,545,254 A | 8/1996 | Chow et al. |
| 5,563,124 A | 10/1996 | Damien et al. |
| 5,573,537 A | 11/1996 | Rogozinski |
| 5,573,771 A | 11/1996 | Geistlich et al. |
| 5,580,353 A | 12/1996 | Mendes et al. |
| 5,591,453 A * | 1/1997 | Ducheyne et al. ............ 424/484 |
| 5,641,502 A | 6/1997 | Skalla et al. |
| 5,645,591 A | 7/1997 | Kuberasampath et al. |
| 5,645,934 A | 7/1997 | Marcolongo et al. |
| 5,676,699 A | 10/1997 | Gogolewski et al. |
| 5,681,872 A | 10/1997 | Erbe |
| 5,707,962 A | 1/1998 | Chen et al. |
| 5,711,960 A | 1/1998 | Shikinami |
| 5,725,590 A | 3/1998 | Maumy et al. |
| 5,728,753 A | 3/1998 | Bonfield et al. |
| 5,733,868 A | 3/1998 | Peterson et al. |
| 5,752,974 A | 5/1998 | Rhee et al. |
| 5,763,416 A | 6/1998 | Bonadio et al. |
| 5,776,193 A | 7/1998 | Kwan et al. |
| 5,788,976 A | 8/1998 | Bradford |
| 5,792,478 A | 8/1998 | Lawin et al. |
| 5,817,327 A * | 10/1998 | Ducheyne et al. ............ 424/425 |
| 5,819,748 A | 10/1998 | Pfirrmann |
| 5,849,331 A * | 12/1998 | Ducheyne et al. ............ 424/484 |
| 5,861,176 A * | 1/1999 | Ducheyne et al. ............ 424/486 |
| 5,863,758 A | 1/1999 | Oppermann et al. |
| 5,871,777 A * | 2/1999 | Ducheyne et al. ............ 424/486 |
| 5,874,109 A * | 2/1999 | Ducheyne et al. ............ 424/486 |
| 5,874,500 A | 2/1999 | Rhee et al. |
| 5,899,939 A | 5/1999 | Boyce et al. |
| 5,906,824 A | 5/1999 | Suzuki et al. |
| 5,914,356 A | 6/1999 | Erbe |
| 5,928,243 A | 7/1999 | Guyer |
| 5,939,039 A | 8/1999 | Sapieszko et al. |
| 5,942,496 A | 8/1999 | Bonadio et al. |
| 5,948,020 A | 9/1999 | Yoon et al. |
| 5,958,441 A | 9/1999 | Oppermann et al. |
| 5,962,427 A | 10/1999 | Goldstein et al. |
| 5,962,549 A | 10/1999 | Bonfield et al. |
| 5,964,809 A | 10/1999 | Lin et al. |
| 5,977,204 A | 11/1999 | Boyan et al. |
| 5,981,825 A | 11/1999 | Brekke |
| 5,984,969 A | 11/1999 | Matthews et al. |
| 6,017,346 A | 1/2000 | Grotz |
| 6,017,366 A | 1/2000 | Berman |
| 6,027,742 A | 2/2000 | Lee et al. |
| 6,045,555 A | 4/2000 | Smith et al. |
| 6,049,026 A | 4/2000 | Muschler |
| 6,051,247 A | 4/2000 | Hench et al. |
| 6,051,648 A | 4/2000 | Rhee et al. |
| 6,071,530 A | 6/2000 | Polson et al. |
| 6,077,989 A | 6/2000 | Kandel et al. |
| 6,083,522 A | 7/2000 | Chu et al. |
| 6,123,731 A | 9/2000 | Boyce et al. |
| 6,123,957 A | 9/2000 | Jernberg |
| 6,136,029 A | 10/2000 | Johnson et al. |
| 6,142,998 A | 11/2000 | Smith et al. |
| 6,165,486 A | 12/2000 | Marra et al. |
| 6,166,130 A | 12/2000 | Rhee et al. |
| 6,180,605 B1 | 1/2001 | Chen et al. |
| 6,180,606 B1 | 1/2001 | Chen et al. |
| 6,187,047 B1 | 2/2001 | Kwan et al. |
| 6,187,290 B1 | 2/2001 | Gilchrist et al. |
| 6,201,039 B1 | 3/2001 | Brown et al. |
| 6,228,386 B1 | 5/2001 | Yang |
| 6,264,701 B1 | 7/2001 | Brekke |
| 6,280,474 B1 | 8/2001 | Cassidy et al. |
| 6,294,041 B1 | 9/2001 | Boyce et al. |
| 6,294,187 B1 | 9/2001 | Boyce et al. |
| 6,299,905 B1 | 10/2001 | Peterson et al. |
| 6,300,315 B1 | 10/2001 | Lin |
| 6,302,913 B1 | 10/2001 | Ripamonti et al. |
| 6,303,138 B1 | 10/2001 | Peterson et al. |
| 6,309,395 B1 | 10/2001 | Smith et al. |
| 6,312,468 B1 | 11/2001 | Best et al. |
| 6,323,278 B2 | 11/2001 | Rhee et al. |
| 6,325,987 B1 | 12/2001 | Sapieszko et al. |
| 6,331,312 B1 | 12/2001 | Lee et al. |
| 6,337,389 B1 | 1/2002 | Wolfinbarger, Jr. |
| 6,338,751 B1 | 1/2002 | Litkowski et al. |
| 6,344,496 B1 | 2/2002 | Niederauer et al. |
| 6,350,284 B1 | 2/2002 | Törmälä et al. |
| 6,383,519 B1 | 5/2002 | Sapieszko et al. |
| 6,413,538 B1 | 7/2002 | Garcia et al. |
| 6,417,166 B2 | 7/2002 | Lin |
| 6,440,444 B2 | 8/2002 | Boyce et al. |
| 6,458,162 B1 | 10/2002 | Koblish et al. |
| 6,458,889 B1 | 10/2002 | Trollsas et al. |
| 6,468,308 B1 | 10/2002 | Kuberasampath et al. |
| 6,478,825 B1 | 11/2002 | Winterbottom et al. |
| 6,482,427 B2 | 11/2002 | Yang |
| 6,517,857 B2 | 2/2003 | Ylänen et al. |
| 6,517,863 B1 | 2/2003 | LaTorre et al. |
| 6,521,246 B2 | 2/2003 | Sapieszko et al. |
| 6,534,591 B2 | 3/2003 | Rhee et al. |
| 6,544,290 B1 | 4/2003 | Lee et al. |
| 6,551,995 B1 | 4/2003 | Oppermann et al. |
| 6,554,862 B2 | 4/2003 | Hays et al. |
| 6,576,015 B2 | 6/2003 | Geistlich et al. |
| 6,579,533 B1 | 6/2003 | Törmälä et al. |
| 6,582,228 B2 | 6/2003 | Ricci et al. |
| 6,582,672 B1 | 6/2003 | Bonfield et al. |
| 6,585,946 B1 | 7/2003 | Bonfield et al. |
| 6,586,388 B2 | 7/2003 | Oppermann et al. |
| 6,599,323 B2 | 7/2003 | Melican et al. |
| 6,599,516 B1 | 7/2003 | Knaack |
| 6,605,117 B2 | 8/2003 | Kuberasampath et al. |
| 6,605,293 B1 | 8/2003 | Giordano et al. |
| 6,607,548 B2 | 8/2003 | Pohjonen et al. |
| 6,616,698 B2 | 9/2003 | Scarborough |
| 6,626,950 B2 | 9/2003 | Brown et al. |
| 6,630,000 B1 | 10/2003 | Bonutti |
| 6,630,153 B2 | 10/2003 | Long et al. |
| 6,638,309 B2 | 10/2003 | Bonutti |
| 6,660,038 B2 | 12/2003 | Boyer, II et al. |
| 6,679,917 B2 | 1/2004 | Ek |
| 6,679,918 B1 | 1/2004 | Benedict et al. |
| 6,692,498 B1 | 2/2004 | Niiranen et al. |
| 6,696,073 B2 | 2/2004 | Boyce et al. |
| 6,702,856 B2 | 3/2004 | Bonutti |

(56) References Cited

U.S. PATENT DOCUMENTS

| | | | |
|---|---|---|---|
| 6,709,744 B1 | 3/2004 | Day et al. |
| 6,723,131 B2 | 4/2004 | Muschler |
| 6,730,252 B1 | 5/2004 | Teoh et al. |
| 6,733,787 B2 | 5/2004 | Peterson et al. |
| 6,736,799 B1 | 5/2004 | Erbe et al. |
| 6,736,853 B2 | 5/2004 | Bonutti |
| 6,743,232 B2 | 6/2004 | Overaker et al. |
| 6,752,834 B2 | 6/2004 | Geistlich et al. |
| 6,755,832 B2 | 6/2004 | Happonen et al. |
| 6,764,517 B2 | 7/2004 | Yamamoto et al. |
| 6,767,369 B2 | 7/2004 | Boyer, II et al. |
| 6,767,550 B1 | 7/2004 | Génin et al. |
| 6,776,938 B2 | 8/2004 | Bonutti |
| 6,808,585 B2 | 10/2004 | Boyce et al. |
| 6,811,570 B1 | 11/2004 | Gehl |
| 6,827,743 B2 | 12/2004 | Eisermann et al. |
| 6,833,408 B2 | 12/2004 | Sehl et al. |
| 6,843,807 B1 | 1/2005 | Boyce et al. |
| 6,844,024 B2 | 1/2005 | Su et al. |
| 6,846,853 B2 | 1/2005 | Shimp |
| 6,849,275 B2 | 2/2005 | Higham |
| 6,852,330 B2 | 2/2005 | Bowman et al. |
| 6,858,042 B2 | 2/2005 | Nadler et al. |
| 6,860,904 B2 | 3/2005 | Bonutti |
| 6,863,899 B2 | 3/2005 | Koblish et al. |
| 6,884,518 B2 | 4/2005 | Aho et al. |
| 6,887,488 B2 | 5/2005 | Cui et al. |
| 6,902,584 B2 | 6/2005 | Kwan et al. |
| 6,905,517 B2 | 6/2005 | Bonutti |
| 6,911,496 B2 | 6/2005 | Rhee et al. |
| 6,916,910 B2 | 7/2005 | Wolfinbarger, Jr. |
| 6,919,308 B2 | 7/2005 | Oppermann et al. |
| 6,923,985 B2 | 8/2005 | Peterson et al. |
| 6,926,903 B2 | 8/2005 | Pirhonen et al. |
| 6,949,251 B2 | 9/2005 | Dalal et al. |
| 6,953,594 B2 | 10/2005 | Lee et al. |
| 6,969,400 B2 | 11/2005 | Rhee et al. |
| 6,989,029 B2 | 1/2006 | Bonutti |
| 6,989,034 B2 | 1/2006 | Hammer et al. |
| 6,990,982 B1 | 1/2006 | Bonutti |
| 6,991,803 B2 | 1/2006 | Sapieszko et al. |
| 7,001,551 B2 | 2/2006 | Meredith |
| 7,004,974 B1 | 2/2006 | Larsson et al. |
| 7,014,659 B2 | 3/2006 | Boyer, II et al. |
| 7,044,972 B2 | 5/2006 | Mathys, Jr. et al. |
| 7,045,125 B2 | 5/2006 | Erbe et al. |
| 7,052,710 B2 | 5/2006 | Giordano et al. |
| 7,060,287 B1 | 6/2006 | Hubbard et al. |
| 7,070,557 B2 | 7/2006 | Bonutti |
| 7,070,722 B1 | 7/2006 | Gilchrist et al. |
| 7,083,672 B2 | 8/2006 | Wagh et al. |
| 7,087,082 B2 | 8/2006 | Paul et al. |
| 7,087,086 B2 | 8/2006 | Li et al. |
| 7,105,182 B2 | 9/2006 | Szymaitis |
| 7,108,721 B2 | 9/2006 | Huckle et al. |
| 7,118,376 B2 | 10/2006 | Jodaikin et al. |
| 7,122,037 B2 | 10/2006 | Happonen et al. |
| 7,122,057 B2 | 10/2006 | Beam et al. |
| 7,122,205 B2 | 10/2006 | Peterson et al. |
| 7,122,356 B2 | 10/2006 | Keogh et al. |
| 7,132,110 B2 | 11/2006 | Kay et al. |
| 7,134,437 B2 | 11/2006 | Bonutti |
| 7,135,025 B2 | 11/2006 | Pohjonen et al. |
| 7,135,180 B2 | 11/2006 | Truong-Le |
| 7,150,879 B1 | 12/2006 | Lee et al. |
| 7,151,135 B2 | 12/2006 | Rhee et al. |
| 7,153,938 B2 | 12/2006 | Kikuchi et al. |
| 7,156,803 B2 | 1/2007 | Voellmicke et al. |
| 7,156,880 B2 | 1/2007 | Evans et al. |
| 7,166,133 B2 | 1/2007 | Evans et al. |
| 7,172,629 B2 | 2/2007 | McKay |
| 7,176,256 B2 | 2/2007 | Rhee et al. |
| 7,176,284 B2 | 2/2007 | Oppermann et al. |
| 7,186,811 B2 | 3/2007 | Lindholm et al. |
| 7,189,263 B2 | 3/2007 | Erbe et al. |
| 7,189,409 B2 | 3/2007 | Pirhonen et al. |
| 7,192,604 B2 | 3/2007 | Brown et al. |
| 7,223,289 B2 | 5/2007 | Trieu et al. |
| 7,230,039 B2 | 6/2007 | Trieu et al. |
| 7,235,079 B2 | 6/2007 | Jensen et al. |
| 7,235,107 B2 | 6/2007 | Evans et al. |
| 7,235,290 B2 | 6/2007 | Vallittu et al. |
| 7,235,527 B2 | 6/2007 | Makishima et al. |
| 7,241,316 B2 | 7/2007 | Evans et al. |
| 7,241,459 B2 | 7/2007 | Fechner et al. |
| 7,258,873 B2 | 8/2007 | Truong-Le et al. |
| 7,270,813 B2 | 9/2007 | Shimp et al. |
| 7,299,805 B2 | 11/2007 | Bonutti |
| 7,300,439 B2 | 11/2007 | May |
| 7,303,814 B2 | 12/2007 | Lamberti et al. |
| 7,318,841 B2 | 1/2008 | Tofighi et al. |
| 7,322,825 B2 | 1/2008 | Szymaitis |
| 7,326,200 B2 | 2/2008 | Trieu et al. |
| 7,329,281 B2 | 2/2008 | Hays et al. |
| 7,341,601 B2 | 3/2008 | Eisermann et al. |
| 7,368,124 B2 | 5/2008 | Chun et al. |
| 7,378,088 B2 | 5/2008 | Kanemaru et al. |
| 7,378,392 B1 | 5/2008 | Hewick et al. |
| 7,381,224 B1 | 6/2008 | Li et al. |
| 7,381,425 B1 | 6/2008 | Truong-Le |
| 7,413,753 B2 | 8/2008 | Li et al. |
| 7,435,764 B2 | 10/2008 | Vallittu et al. |
| 7,449,498 B2 | 11/2008 | Park et al. |
| 7,455,854 B2 | 11/2008 | Gower et al. |
| 7,462,200 B2 | 12/2008 | Bonutti |
| 7,473,277 B2 | 1/2009 | Boyer, II et al. |
| 7,485,617 B1 | 2/2009 | Pohl et al. |
| 7,494,950 B2 | 2/2009 | Armitage et al. |
| 7,510,579 B2 | 3/2009 | Preissman |
| 7,514,248 B2 | 4/2009 | Gower et al. |
| 7,514,249 B2 | 4/2009 | Gower et al. |
| 7,531,004 B2 | 5/2009 | Bagga et al. |
| 7,534,451 B2 | 5/2009 | Erbe et al. |
| 7,544,196 B2 | 6/2009 | Bagga et al. |
| 7,544,212 B2 | 6/2009 | Li et al. |
| 7,544,496 B2 | 6/2009 | Gower et al. |
| 7,547,449 B2 | 6/2009 | Gower et al. |
| 7,563,455 B2 | 7/2009 | McKay |
| 7,578,845 B2 | 8/2009 | Nies et al. |
| RE41,286 E | 4/2010 | Atkinson et al. |
| 7,700,819 B2 | 4/2010 | Ambrosio et al. |
| 7,718,616 B2 | 5/2010 | Thorne |
| 7,722,895 B1 | 5/2010 | McKay et al. |
| 7,723,291 B2 | 5/2010 | Beals et al. |
| 7,727,283 B2 | 6/2010 | Bonutti |
| 7,740,897 B2 | 6/2010 | Marx et al. |
| 7,767,221 B2 | 8/2010 | Lu et al. |
| 7,771,755 B2 | 8/2010 | Li et al. |
| 7,815,926 B2 | 10/2010 | Syring et al. |
| 7,824,703 B2 | 11/2010 | Scifert et al. |
| 7,837,740 B2 | 11/2010 | Semler et al. |
| 7,842,097 B2 | 11/2010 | Yamamoto et al. |
| 7,847,072 B2 | 12/2010 | Thorne |
| 7,883,693 B2 | 2/2011 | Sehl et al. |
| 7,883,694 B2 | 2/2011 | Rhee et al. |
| 7,887,598 B2 | 2/2011 | Evans et al. |
| 7,892,291 B2 | 2/2011 | Evans et al. |
| 7,896,880 B2 | 3/2011 | Bonutti |
| 7,901,457 B2 | 3/2011 | Truncale et al. |
| 7,932,354 B2 | 4/2011 | Heimann et al. |
| 7,939,108 B2 | 5/2011 | Morris et al. |
| 7,943,112 B2 | 5/2011 | Mao et al. |
| 7,959,941 B2 | 6/2011 | Knaack et al. |
| 7,968,110 B2 | 6/2011 | Hubbard |
| 7,998,499 B2 | 8/2011 | Li et al. |
| 8,002,813 B2 | 8/2011 | Scarborough et al. |
| 8,008,357 B2 | 8/2011 | Shoji et al. |
| 8,067,027 B2 | 11/2011 | Hubbard |
| 8,067,031 B2 | 11/2011 | Daniloff et al. |
| 8,101,676 B2 | 1/2012 | McKay |
| 8,114,841 B2 | 2/2012 | Lynch et al. |
| 8,163,032 B2 | 4/2012 | Evans et al. |
| 8,197,474 B2 | 6/2012 | Scarborough et al. |
| 8,197,802 B2 | 6/2012 | Rhee et al. |

(56) References Cited

U.S. PATENT DOCUMENTS

| | | | |
|---|---|---|---|
| 8,221,500 B2 | 7/2012 | Truncale et al. | |
| 8,287,915 B2 | 10/2012 | Clineff et al. | |
| 8,303,967 B2 | 11/2012 | Clineff et al. | |
| 8,303,976 B2 | 11/2012 | Sapieszko et al. | |
| 8,377,466 B2 | 2/2013 | Sehl et al. | |
| 8,506,985 B2* | 8/2013 | Garcia De Castro Andrews et al. | 424/426 |
| 8,551,525 B2 | 10/2013 | Cook et al. | |
| 8,778,378 B2* | 7/2014 | Clineff et al. | 424/423 |
| 2002/0018796 A1 | 2/2002 | Wironen | |
| 2002/0076429 A1 | 6/2002 | Wironen et al. | |
| 2002/0098222 A1 | 7/2002 | Wironen et al. | |
| 2002/0193338 A1 | 12/2002 | Goldstein et al. | |
| 2003/0009235 A1 | 1/2003 | Manrique et al. | |
| 2003/0039676 A1 | 2/2003 | Boyce et al. | |
| 2003/0055512 A1 | 3/2003 | Genin et al. | |
| 2003/0095997 A1 | 5/2003 | Ruszczak et al. | |
| 2003/0143255 A1 | 7/2003 | Aho et al. | |
| 2003/0148979 A1 | 8/2003 | Sosnowski et al. | |
| 2003/0180344 A1 | 9/2003 | Wise et al. | |
| 2003/0180376 A1 | 9/2003 | Dalal et al. | |
| 2003/0193104 A1 | 10/2003 | Melican et al. | |
| 2004/0052861 A1 | 3/2004 | Hatcher et al. | |
| 2004/0078090 A1 | 4/2004 | Binette et al. | |
| 2004/0115240 A1 | 6/2004 | Narhi et al. | |
| 2004/0220680 A1 | 11/2004 | Yamamoto et al. | |
| 2005/0074481 A1 | 4/2005 | Brekke et al. | |
| 2005/0118230 A1 | 6/2005 | Hill et al. | |
| 2005/0186240 A1 | 8/2005 | Ringeisen et al. | |
| 2005/0288795 A1 | 12/2005 | Bagga et al. | |
| 2006/0018942 A1 | 1/2006 | Rowe et al. | |
| 2006/0030948 A1 | 2/2006 | Manrique et al. | |
| 2006/0067967 A1 | 3/2006 | Bowman et al. | |
| 2006/0067969 A1 | 3/2006 | Lu et al. | |
| 2006/0195179 A1 | 8/2006 | Sun et al. | |
| 2006/0212125 A1 | 9/2006 | Okihana | |
| 2006/0246150 A1 | 11/2006 | Thorne | |
| 2006/0251729 A1 | 11/2006 | Kay et al. | |
| 2006/0252981 A1 | 11/2006 | Matsuda et al. | |
| 2006/0292670 A1 | 12/2006 | Ting et al. | |
| 2006/0293760 A1 | 12/2006 | DeDeyne | |
| 2007/0003593 A1 | 1/2007 | Wironen et al. | |
| 2007/0026030 A1 | 2/2007 | Gill et al. | |
| 2007/0026069 A1 | 2/2007 | Shastri et al. | |
| 2007/0031470 A1 | 2/2007 | Kladakis et al. | |
| 2007/0088437 A1 | 4/2007 | Betz et al. | |
| 2007/0122447 A1 | 5/2007 | Koblish et al. | |
| 2007/0134285 A1 | 6/2007 | Lynn et al. | |
| 2007/0166348 A1 | 7/2007 | Van Dyke | |
| 2007/0190101 A1 | 8/2007 | Yang et al. | |
| 2007/0191851 A1 | 8/2007 | Ashammakhi | |
| 2007/0191963 A1 | 8/2007 | Winterbottom et al. | |
| 2007/0202148 A1 | 8/2007 | Ringeisen et al. | |
| 2008/0033572 A1 | 2/2008 | D'Antonio et al. | |
| 2008/0069852 A1 | 3/2008 | Shimp et al. | |
| 2008/0075749 A1 | 3/2008 | Dyer | |
| 2008/0187571 A1 | 8/2008 | Clineff et al. | |
| 2008/0249637 A1 | 10/2008 | Asgari | |
| 2009/0022771 A1 | 1/2009 | Lynn et al. | |
| 2009/0030528 A1 | 1/2009 | Evans et al. | |
| 2009/0076624 A1 | 3/2009 | Rahaman et al. | |
| 2009/0110743 A1 | 4/2009 | Dalal et al. | |
| 2009/0123547 A1 | 5/2009 | Hill et al. | |
| 2009/0198167 A1 | 8/2009 | Ambrosio | |
| 2009/0222090 A1 | 9/2009 | Mayr et al. | |
| 2009/0254194 A1 | 10/2009 | Peters et al. | |
| 2009/0317447 A1 | 12/2009 | Hsiao et al. | |
| 2009/0318982 A1 | 12/2009 | Genin et al. | |
| 2010/0086598 A1 | 4/2010 | Sosnowski et al. | |
| 2010/0119492 A1 | 5/2010 | Hans et al. | |
| 2010/0226961 A1 | 9/2010 | Lamberti et al. | |
| 2011/0150963 A1* | 6/2011 | Clineff et al. | 424/423 |
| 2011/0151027 A1 | 6/2011 | Clineff et al. | |

OTHER PUBLICATIONS

Schepers, E. et al., "Bioactive glass particulate material as a filler for bone lesions", Journal of Oral Rehabilitation, vol. 18, 1991, pp. 439-452.

El-Ghannam, A., "Bone reconstruction—from bioceramics to tissue engineering", Expert Rev. Med. Devices, vol. 2, No. 1, 2005, pp. 87-101.

Santos, F. et al., "Comparison of Biomaterial Implants in the Dental Socket: Histological Analysis in Dogs", Clinical Implant Dentistry and Related Research, vol. 12, No. 1, 2010, pp. 18-25.

Schwartz, Z. et al., "Differential effects of bone graft substitutes on regeneration of bone marrow", Clin. Oral Impl. Res., vol. 19, 2008, pp. 1233-1245.

Moreira-Gonzalez, A. et al., "Evaluation of 45S5 Bioactive Glass Combined as a Bone Substitute in the Reconstruction of Critical Size Calvarial Defects in Rabbits", The Journal of Craniofacial Surgery, vol. 16, No. 1, Jan. 2005, pp. 63-70. .

Andrade, A. et al., "In Vivo Performance of a Sol-Gel Glass-Coated Collagen", Journal of Biomedical Materials Research Part B: Applied Biomaterials, pp. 122-128, (2006).

Hertz, A. et al., "Inorganic materials for bone repair or replacement applications", Nanomedicine, vol. 2, No. 6, 2007, pp. 899-918.

Phan, P. et al., "The effect of silica-containing calcium-phosphate particles on human osteoblasts in vitro", Silica-Containing Bioactive Ceramics, 2003, pp. 1001-1008.

Ladd, A. et al., "Use of Bone-Graft Substitutes in Distal Radius Fractures", Journal of the American Academy of Orthopedic Surgeons, vol. 7, No. 5, Sep./Oct. 1999, pp. 279-290.

Veron, C. et al., "A panorama of current materials for osseous application in maxillofacial surgery and oral implantology", Revue de Stomatologie et de Chirurgie Maxillo-fac., vol. 96, No. 4, 1995, pp. 274-281.

Lickorish, D. et al., "Collagen-hydroxyapatite composite prepared by biomimetic process", Journal of Biomedical Materials Research: Part A, 2004, pp. 19-27.

Lu, H. et al., "Three-dimensional, bioactive, biodegradable, polymer-bioactive glass composite scaffolds with improved mechanical properties support collagen synthesis and mineralization of human osteoblast-like cells in vitro", Journal of Biomedical Materials Research: Part A, 2003, pp. 465-474.

Lee, S. et al., "Investigation of bone formation using calcium phosphate glass cement in beagle dogs", Journal of Periodontal and Implant Science, vol. 40, 2010, pp. 125-131.

Martin, R. B., "Bone as a Ceramic Composite Material", Materials Science Forum, vol. 293 (1999) 13 pages.

Song, Ju-Ha et al., "Collagen-Hydroxyapatite Membranes for Guided Bone Regeneration," (abstract) [retrieved on Sep. 23, 2010]. Retrieved from the Internet: http://www.biomaterials.org/abstracts/data/papers/2006/495.pdf.

Stanishevsky, A. et al., "The Relationship between the Ceramic Nanoparticle Loading and Mechanical Properties of Collagen/Hydroxyapatite Nanoparticle Composites," (abstract) [retrieved on Sep. 23, 2010]. Retrieved from the Internet: http://www.biomaterials.org/abstracts/data/papers/2007/468.pdf.

Kim et al., "Bioactive glass nanofiber-collagen nanocomposite as a novel bone regeneration matrix," J. Biomed. Mater. Res. Part A, (2006) vol. 79, pp. 698-705.

* cited by examiner

BONE GRAFT MATERIALS AND METHODS

CROSS REFERENCE TO OTHER APPLICATIONS

This application is a continuation of and claims priority to U.S. patent application Ser. No. 12/977,191, filed Dec. 23, 2010 (now U.S. Pat. No. 8,551,525), entitled "Bone Graft Materials and Methods," the disclosure of which is incorporated by reference herein in its entirety.

BACKGROUND

The present invention generally relates to bone grafting, and more particularly to repairing and/or filling a void or gap in a bone or bony structure of a patient.

A need exists for improved bone graft materials. Current bone grafting includes the use of autogenous bone as a graft material (i.e., "autografting"). Use of autogenous bone, however, subjects a patient to increased pain and discomfort, and an increased risk of infection, because it requires the patient undergo surgery to recover the autogenous bone for use in the grafting procedure. Current bone grafting also includes the use of bone from a donor as a graft material (e.g., "allografting" from the same species or "xenografting" from a different species). Both allograft bone and xenograft bone, though from natural sources, subject a patient to the risk of disease transmission and graft rejection.

Current bone grafting further includes the use of synthetic bone graft material. Some such synthetic bone graft material is mixed with autograft, allograft, or xenograft bone, and thus still subjects a patient to the risks above. Other disadvantages to current synthetic bone graft material are the lack of sufficient resorbability, lack of sufficient porosity, and increased manufacturing costs due to a high number of component materials. As such, there is a need for an improved synthetic bone graft material that is resorbable and porous, and that helps to reduce manufacturing costs by reducing the number of component materials.

SUMMARY OF THE INVENTION

Compositions, materials, methods and kits for bone grafting are described. In some embodiments, a bone graft composition includes about 15% to about 20% by weight collagen, about 55% to about 70% by weight bioactive glass, and about 15% to about 30% by weight a calcium phosphate. The bioactive glass and the calcium phosphate together are about 80% to about 85% by weight of the bone graft composition. In some embodiments, a bone graft composition includes a collagen matrix and a plurality of bioactive glass particulates dispersed throughout the collagen matrix. A majority of the bioactive glass particulates are about 53 µm to about 425 µm in size. The collagen matrix is about 20% to about 60% by weight of the bone graft composition, and the bioactive glass is about 40% to about 80% by weight of the bone graft composition.

DETAILED DESCRIPTION

Figure 1A:
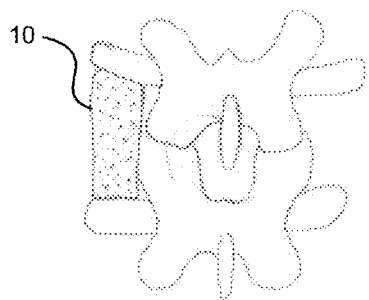
FIG. 1A is a posterior view of a bone graft composition according to an embodiment implanted between transverse processes of vertebra.

Compositions, materials, methods and kits for bone grafting, including for repairing and/or filling a void or gap in a bone or other bony structure of a patient, are described herein. Also described herein are methods for preparing such compositions and materials.

As used in this specification, the singular forms "a," "an" and "the" include plural referents unless the context clearly dictates otherwise. Thus, for example, the term "a material" is intended to mean one or more materials, or a combination thereof.

As used herein, the term "biocompatible" refers to the ability (e.g., of a composition or material) to perform with an appropriate host response in a specific application, or at least to perform without having a toxic or otherwise deleterious effect on a biological system of the host, locally or systemically.

As used herein, the term "osteoconductive" refers to the ability (e.g., of a composition or material) to passively permit bone growth (e.g., onto and/or into the material). As such, osteoconduction can be characterized as a passive process. A material (e.g., a graft or implant) can be osteoconductive, for example, because it is configured to passively permit growth of bone on a surface of the material. In another example, a material can be osteoconductive because it is configured to passively permit growth of bone into an opening (e.g., a pore) of the material.

As used herein, the term "osteoinductive" refers to the capability (e.g., of a composition or material) to actively stimulate a biological response which induces bone formation. As such, osteoinduction can be characterized as an active process. Osteoinduction can include the formation and/or stimulation of osteoprogenitor cells, such as osteoprogenitor cells in bodily tissue surrounding or proximate to a graft or implant.

As used herein, the term "biodegradable" refers to the capability of a material to be degraded, disassembled, and/or digested over time by action of a biological environment (including the action of living organisms, e.g., the patient's body) and/or in response to a change in physiological pH or temperature. As used herein, the term "resorbable" refers to the capability of a material to be broken down over a period of time and assimilated into the biological environment.

As used herein, references to a weight of components of a bone graft composition or material described herein, such as the phrase "by weight," refer to the weight of the applicable component prior to being added to or mixed with another different component of the bone graft composition. For example, the weight can refer to an initial weight of the component measured out before further processing of the component into the bone graft composition.

As used herein, the term "fibrillar" refers to being in the form of fibrils, and not in the form of fibers. For example, a reference to collagen in the fibrillar form includes collagen fibrils, but not native collagen fibers.

As used herein, the phrase "non-load bearing application" refers to an application for repair of a void or gap in a bone or another bony structure in which the void or gap to be repaired is not intrinsic to the stability of the bone or bony structure.

A bone graft composition (or material) according to an embodiment is configured to facilitate repair or regeneration of bone at a target repair site. For example, in some embodiments, the bone graft composition can be osteoconductive, osteoinductive, or both. The target repair site can be, for example, a void, gap, or other defect in a bone or other bony structure in a body of a patient. For example, as described in more detail below, the bone graft composition can be configured to facilitate bone growth at a target repair site in the spine, pelvis, an extremity, the cranium, or another bone or bony structure in the patient's body. The bone graft composition is configured to be implanted or otherwise disposed at the target repair site. For example, in some embodiments, the bone graft composition is configured to be implanted or disposed at the target repair site in a non-load bearing application.

The bone graft composition can include various combinations of collagen, bioactive glass, and calcium phosphate, each of which components is described in more detail herein. The bone graft composition is biocompatible. The bone graft composition is biodegradable. More specifically, in some embodiments, at least a portion of the bone graft composition is resorbable. For example, at least one of the collagen, bioactive glass, and calcium phosphate, or a combination thereof, can be resorbable. In some embodiments, the bone graft composition is, as a whole, resorbable.

The collagen can be or include soluble collagen, insoluble collagen, or a combination thereof. The collagen can be or include type I collagen, type II collagen, type III collagen, type VII collagen, another suitable type of collagen, or a combination thereof. For example, in some embodiments, the collagen is or includes medical grade type I collagen. In some embodiments, the collagen includes type I collagen and up to about 5% of a type of collagen different than type I collagen. For example, the collagen can include type I collagen and up to about 5% type III collagen. Specifically, the collagen can include about 5% type III collagen and the remainder of the collagen is type I collagen. In another example, the collagen can include type I collagen and up to about 5% type VII collagen. The collagen can be human, equine, bovine, porcine, murine, synthetic, or from another suitable source. For example, the collagen can be derived from bovine corneum.

In some embodiments, the collagen is in fibrillar form. In some embodiments, at least prior to being implanted into the body of the patient, the collagen is not mineralized. In some embodiments, the collagen is uncompressed. In this manner, because the collagen is uncompressed, the bone graft composition can also be characterized as being uncompressed.

The collagen of the bone graft composition can be a matrix in and/or on which the bioactive glass and calcium phosphate are disposed. In this manner, the collagen matrix facilitates delivery of the bioactive glass and calcium phosphate to the target repair site. The collagen matrix of the bone graft composition can be in any suitable form. For example, in some embodiments, the collagen matrix is in a flowable form. Suitable flowable forms include a slurry, foam, gel, or paste. In this manner, at least one of the bioactive glass and/or calcium phosphate can be mixed with and/or embedded into the flowable collagen matrix. In some embodiments, the collagen matrix is a hardened, brittle, or otherwise dry cracker-like material. For example, the collagen matrix can be formed by drying the flowable collagen, as described in more detail below. At least a portion of the bioactive glass and/or the calcium phosphate can disposed (e.g., sprinkled or otherwise coated) onto a surface of the dried collagen matrix. In some embodiments, the collagen matrix is in a sponge-like form. For example, the dried collagen matrix can be wetted with a suitable solution to form a sponge-like collagen matrix. Suitable solutions include, but are not limited to, blood, marrow, another bodily fluid, a simulated body fluid, saline, phosphate buffered saline, gel, or another biocompatible fluid, or any combination of the foregoing. In some embodiments, the dried collagen can be wetted with a solution that includes at least one of the bioactive glass or calcium phosphate. The collagen matrix, in any suitable form generally and in the dry or sponge-like form particularly, includes a surface configured to receive bioactive glass and/or calcium phosphate, for example, in granular or particulate form.

Figure 2A:
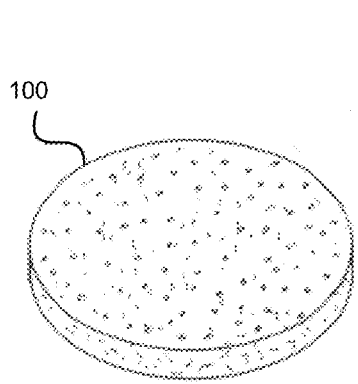
FIG. 2A is a perspective view of a bone graft material according to an embodiment.
Figure 2B:
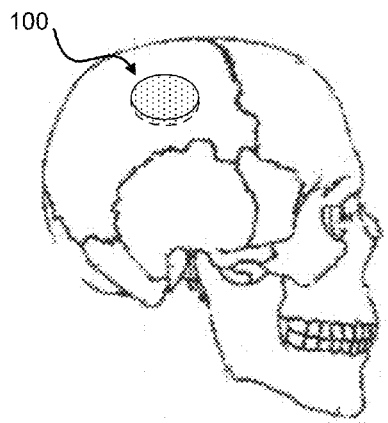
FIG. 2B is the bone graft material of FIG. 2A implanted into a bone void in a cranium.

The collagen matrix of the bone graft composition is porous. In some embodiments, the collagen matrix defines a plurality of pores (e.g., as shown in FIGS. 2A-2B with respect to an implant 100). At least a portion of the pores can be configured to permit the in-growth of bone. In this manner, the collagen matrix, and thus the bone graft composition, is osteoconductive. The porosity of the collagen matrix can be in any suitable range. For example, in some embodiments, the bone graft composition has a porosity within the range of about 50% to about 95%. In some embodiments, the bone graft composition has a porosity within the range of about 70% to about 90%. More specifically, in some embodiments, the bone graft composition is about 70% porous.

The pores of the collagen matrix can be any suitable size(s) for permitting bone growth therein. For example, in some embodiments, the pores of the collagen matrix each have a diameter greater than about 100 μm. In other embodiments, the collagen matrix defines pores each having a diameter less than about 100 μm. The collagen matrix can define pores of various sizes. For example, in some embodiments, a first portion of pores of the plurality each have a diameter greater than about 100 μm and a second portion of pores of the plurality each have a diameter less than about 100 μm. In some embodiments, at least a portion of the plurality of pores of the composition are interconnected, which can further facilitate the in-growth of bone.

The bioactive glass of the bone graft composition is configured to facilitate the regrowth of bone at the target repair site. In some embodiments, the bioactive glass of the bone graft composition can be an osteoconductive agent. As described above, the bioactive glass can be disposed on, embedded within, and or mixed with the collagen of the bone graft material. In some embodiments, the bioactive glass can be mixed with the collagen such that the bioactive glass is randomly dispersed throughout the collagen. For example, the bioactive glass can be mixed with the collagen to form a substantially homogenous mixture (e.g., a slurry) of collagen and bioactive glass. In some embodiments, the bioactive glass is disposed on (e.g., coated or sprinkled onto) a surface of the collagen (e.g., the collagen matrix in one of the flowable, dried, or sponge-like forms).

The bioactive glass can be any alkali-containing ceramic, glass, glass-ceramic, or crystalline material that facilitates bone formation after contact with a biological environment. Suitable bioactive glass can include 45S5, 58S, S70C30, or a combination of the foregoing bioactive glasses. Specifically, in some embodiments, the bioactive glass is a 45S5 Bioglass with a nominal chemical composition of 45% silicon dioxide ($SiO_2$) (±2%), 24.5% calcium oxide (CaO) (±2%), 24.5% sodium oxide ($Na_2O$) (±2%), and 6% phosphorous pentoxide ($P_2O_5$) (±1%). The bioactive glass can include trace or minimal amounts of at least one heavy element, including, but not limited to, arsenic (As), cadmium (Cd), mercury (Hg), lead (Pb), or a combination thereof. For example, the bioactive glass can include As in an amount less than about 3 parts per million (ppm). In another example, the bioactive glass can include Cd in an amount less than about 5 ppm. In yet another example, the bioactive glass can include Hg in an amount less than about 5 ppm. In still another example, the bioactive glass can include Pb in an amount less than about 30 ppm. Specifically, in some embodiments, the bioactive glass is a 45S5 Bioglass of the composition described above and including 3 ppm As, 5 ppm Cd, 5 ppm Hg, and 30 ppm Pb.

The bioactive glass can be in any suitable form. For example, in some embodiments, the bioactive glass is in particulate form. In the particulate form, the bioactive glass particles are discrete and generally not interconnected. As such, the bioactive glass particles, collectively, are generally amorphous. In other words, the bioactive glass particles, collectively, generally lack an intentional structure or organization. The bioactive glass particles can be generally irregular in shape. The bioactive glass particles can have a smooth surface.

The bioactive glass particles can be any suitable size. In some embodiments, at least a portion of the bioactive glass particles are within a range of about 53 μm to about 425 μm. In some embodiments, the bioactive glass includes particles within a range of about 212 μm to about 425 μm. For example, in some embodiments, at least 85% of the bioactive glass are particles within a range of about 212 μm to about 425 μm. The bioactive glass can include particles of various sizes; for example, of various sizes within at least one of the foregoing ranges. In some embodiments, the bioactive glass particles are sufficiently large to prevent the particles from leaching out of the collagen carrier, e.g., when the dried collagen is wetted with a solution.

Any suitable method of measuring the bioactive glass particle size may be used. For example, the bioactive glass particles can be sieved using American Society for Testing and Materials ("ASTM" )sieves according to ASTM E 11-70 (1995) method. When using such a method, for example, particles (or granules) retained between 40 and 70 mesh can be used in the bone graft composition. Because particles screened within a certain range may contain a small amount of smaller particles due to screen blinding, a precision screen may be used to determine the amount of particles within the desired particle size range.

The calcium phosphate of the bone graft composition is also configured to facilitate the regrowth of bone at the target repair site. In some embodiments, the calcium phosphate of the bone graft composition is an osteoinductive agent. The calcium phosphate is configured to be disposed on, embedded in, or otherwise mixed with the collagen. In some embodiments, the calcium phosphate can be mixed with the collagen such that the calcium phosphate is randomly dispersed throughout the collagen. For example, the calcium phosphate can be mixed with the collagen to form a substantially homogenous mixture (e.g., a slurry) of collagen and calcium phosphate. In another example, the calcium phosphate can be mixed with the collagen and the bioactive glass.

The calcium phosphate can include any suitable calcium phosphate or mineral thereof, including, but not limited to, hydroxyapatite (sometimes referred to as hydroxylapatite; also referred to herein as "HA"), tricalcium phosphate (also referred to herein as "TCP"), or a combination of the foregoing. In some embodiments, the calcium phosphate is biphasic and includes tricalcium phosphate and hydroxyapatite. For example, the calcium phosphate can include about 40% to about 80% by weight tricalcium phosphate and about 20% to about 60% by weight hydroxyapatite. More specifically, in some embodiments, the calcium phosphate includes about 80% tricalcium phosphate and about 20% hydroxyapatite. In other embodiments, the calcium phosphate includes about 60% tricalcium phosphate and about 40% hydroxyapatite. In yet other embodiments, the calcium phosphate includes about 40% tricalcium phosphate and about 60% hydroxyapatite.

The calcium phosphate can be in any suitable form. For example, the calcium phosphate can be in particulate or granular form. The calcium phosphate can be of any suitable size. For example, in some embodiments, the calcium phosphate includes mineral particles within the range of about 200 μm to about 2 mm in size. In some embodiments, the calcium phosphate includes mineral particles within the range of about 200 μm to about 800 μm in size. In some embodiments, the calcium phosphate includes mineral particles within the range of about 0.5 mm to about 1 mm in size.

Bone graft compositions of various weight ratios of collagen, bioactive glass, and calcium phosphate are contemplated. In some embodiments, a bone graft composition includes about 10% to about 20% by weight collagen, about 25% to about 80% bioactive glass, and about 5% to about 60% calcium phosphate. More specifically, a bone graft composition according to an embodiment includes about 15% to about 20% by weight collagen, about 55% to about 70% by weight bioactive glass, and about 15% to about 30% by weight calcium phosphate. The bioactive glass and the calcium phosphate together comprise about 80% to about 85% by weight of the bone graft composition.

In some embodiments, for example, the bone graft composition can include about 15% by weight collagen, about 55% to about 65% by weight bioactive glass, and about 20% to about 30% by weight calcium phosphate. In another example, the bone graft composition can include about 15% collagen, about 55% bioactive glass, and about 30% calcium phosphate, such that a weight ratio of the collagen to the bioactive glass to the calcium phosphate is about 15%:55%:30%, respectively.

In yet another example, the bone graft composition can include about 15% collagen, about 60% bioactive glass, and about 25% calcium phosphate, such that a weight ratio of the collagen to the bioactive glass to the calcium phosphate is about 15%:60%:25%, respectively. In still another example, the bone graft composition can include about 15% collagen, about 65% bioactive glass, and about 20% calcium phosphate, such that a weight ratio of the collagen to the bioactive glass to the calcium phosphate is about 15%:65%:20%, respectively.

In other embodiments, the bone graft composition can include about 20% by weight collagen, about 50% to about 60% by weight bioactive glass, and about 20% to about 30% by weight calcium phosphate. For example, the bone graft composition can include about 20% collagen, about 50% bioactive glass, and about 30% calcium phosphate, such that a weight ratio of the collagen to the bioactive glass to the calcium phosphate is about 20%:50%:30%, respectively.

In another example, the bone graft composition can include about 20% collagen, about 55% bioactive glass, and about 25% calcium phosphate, such that a weight ratio of the collagen to the bioactive glass to the calcium phosphate is about 20%:55%:25%, respectively. In still another example, the bone graft composition can include about 20% collagen, about 60% bioactive glass, and about 20% calcium phosphate, such that a weight ratio of the collagen to the bioactive glass to the calcium phosphate is about 20%:60%:20%, respectively. In some embodiments, the collagen, bioactive glass, and calcium phosphate collectively comprise 100% by weight of the bone graft composition.

In the foregoing examples, the collagen, bioactive glass, and calcium phosphate can be any collagen, bioactive glass, and calcium phosphate, respectively, described herein. For example, the collagen can be medical grade type I collagen. In another example, the calcium phosphate can include about 40% to about 80% tricalcium phosphate and about 20% to about 60% hydroxyapatite.

Although the bone graft compositions have been described above as including collagen, bioactive glass, and calcium phosphate, in some embodiments, a bone graft composition includes collagen and bioactive glass. For example, a bone graft composition according to another embodiment includes a collagen matrix and a plurality of bioactive glass particulates. The collagen matrix can include any collagen described herein, or of a combination of any collagen described herein. For example, the collagen matrix can be or include type I collagen. In another example, the collagen matrix can be or include a combination of type I collagen and type III collagen. The collagen matrix can be in any suitable form. For example, in some embodiments, the collagen matrix is in a flowable form (e.g., a slurry, foam, gel, or paste), a dried form, or a sponge-like form, as described above. In some embodiments, the plurality of bioactive glass particulates is dispersed throughout the collagen matrix. The bioactive glass can be any bioactive glass described herein. For example, in some embodiments, a majority of the plurality of bioactive glass particulates are within a range of about 53 μm to about 425 μm in size. More specifically, in some embodiments, the majority of the bioactive glass particulates can be within a range of about 212 μm to about 425 μm in size. Still more specifically, in some embodiments, at least 85% of the plurality of bioactive glass particulates can be within the range of about 212 μm to about 425 μm in size.

Bone graft compositions of various ratios of collagen and bioactive glass are contemplated. In some embodiments, the bone graft composition includes, by weight, about 20% to about 60% collagen matrix and about 40% to about 80% bioactive glass. More specifically, for example, the collagen matrix can be about 20% by weight of the bone graft composition and the plurality of bioactive glass particulates can be about 80% by weight of the bone graft composition. In another example, the collagen matrix can be about 40% by weight of the bone graft composition and the plurality of bioactive glass particulates can be about 60% by weight of the bone graft composition. In yet another example, the collagen matrix can be about 60% by weight of the bone graft composition and the plurality of bioactive glass particulates can be about 40% by weight of the bone graft composition.

In some embodiments, the collagen matrix and the plurality of bioactive glass particulates collectively comprise 100% by weight of the bone graft composition. In embodiments in which the collagen and bioactive glass comprise 100% of the bone graft composition, the bone graft composition is, prior to implantation into the patient's body, free of additional components including, but not limited to, bone or forms thereof (e.g., bone particles, bone powder, demineralized bone matrix), cells, tissue particles, blood products, calcium phosphate, rubber, gelatin, bone morphogenetic proteins, growth factors, anti-inflammatory agents, drugs, and radiopaque particles.

As noted above, a bone graft composition according to an embodiment can be configured for use at various target repair sites within a body of a patient to facilitate bone growth therein. In some embodiments, the bone graft composition is configured for use at a target repair site in the patient's spine.

Figure 1B:
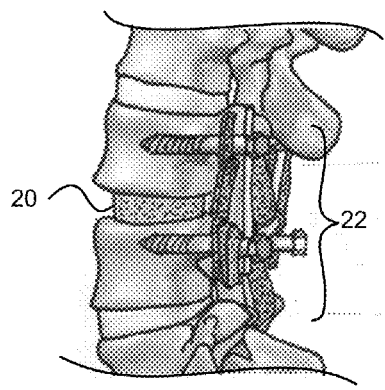
FIG. 1B is a side view of bone graft compositions according to embodiments disposed between vertebral bodies and on posterior portions of vertebrae.
Figure 1C:
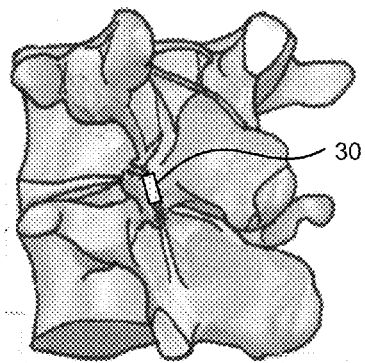
FIG. 1C is a side view of a bone graft composition according to an embodiment disposed proximate to a facet joint of a spine.

For example, as shown in FIG. 1A, a bone graft composition 10 can be disposed in an opening between a transverse process of a first vertebra and a transverse process of a second vertebra. In this manner, the bone graft composition can facilitate growth of a bony bridge between the transverse processes of the first and second vertebrae, such as to achieve posterolateral spinal fusion. In another example, as shown in FIG. 1B, a bone graft composition 20 can be disposed in a void or opening between a body of a first vertebra and a body of a second vertebra different than the first vertebra. In this manner, for example, the bone graft composition can facilitate growth of bone between the body of the first vertebra and the body of the second vertebra to achieve interbody fusion of the vertebrae. Referring again to FIG. 1B, in some embodiments, a plurality of bone graft composition implants 22 can be positioned adjacent a posterior portion of the spine, for example, to facilitate growth of a bony bridge between adjacent vertebrae. In this manner, the plurality of bone graft composition implants 22 can facilitate fusion of the adjacent vertebrae. In some embodiments, such as in a spinal fusion procedure, the bone graft composition is used in conjunction with a mechanical support (e.g., a plurality of screws and/or rods, as shown in FIG. 1B). In still another example, referring to FIG. 1C, a bone graft composition 30 can be implantable in or proximate to a facet joint of adjacent vertebrae to facilitate growth of bone at the facet joint.

Figure 1D:
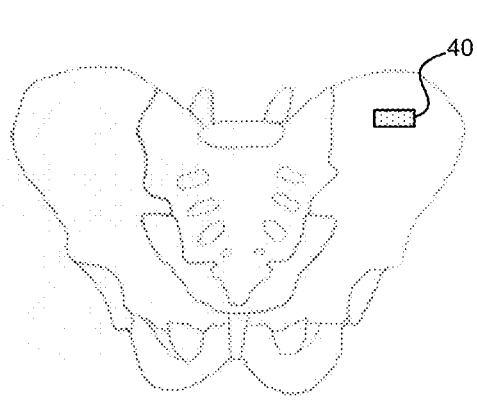
FIG. 1D is an anterior view of a bone graft composition according to an embodiment disposed on an ilium.
Figure 1E:
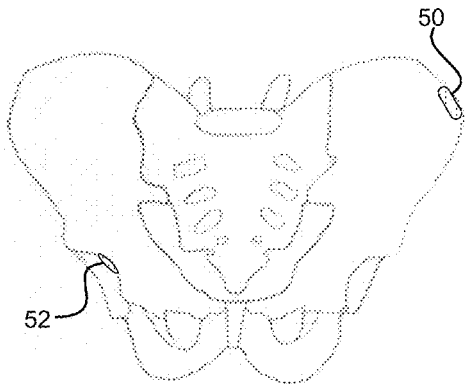
FIG. 1E is an anterior view of bone graft compositions according to embodiments disposed at an iliac crest and an acetabulum.

In some embodiments, a bone graft composition is configured for use at a target repair site in the patient's pelvis. For example, as shown in FIG. 1D, a bone graft composition 40 can be disposed in an opening in the patient's ilium. In some embodiments, a bone graft composition is configured to be disposed in or at a target repair site at a different portion of the pelvis, such as, for example, the iliac crest (e.g., bone graft composition 50 shown in FIG. 1E), acetabulum (e.g., bone graft composition 52 shown in FIG. 1E), ischium, or pubis.

Figure 1F:
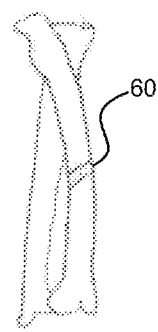
FIG. 1F is a side view of a bone graft composition according to an embodiment disposed in a radius (which is shown adjacent an ulna).
Figure 1G:
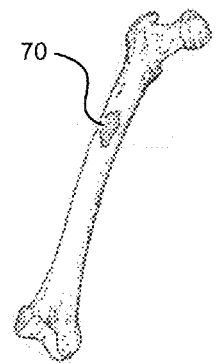
FIG. 1G is a perspective view of a bone graft composition according to an embodiment disposed in a femur.
Figure 1H:
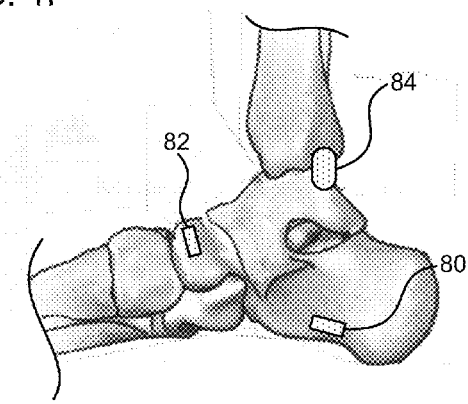
FIG. 1H is a side view of bone graft compositions according to embodiments disposed on bones of a foot and at an ankle joint.

In some embodiments, a bone graft composition is configured for use at a target repair site in a bone of an extremity of the patient. For example, a bone graft composition can be configured to be disposed in an opening in the radius (e.g., bone graft composition 60 in FIG. 1F), ulna, humerus, tibia, fibula, femur (e.g., bone graft composition 70 in FIG. 1G), or other bone of an extremity. In another example, the bone graft composition can be configured to be disposed in an opening in a knee joint. In yet another example, referring to FIG. 1H, a bone graft composition is configured to be disposed in an opening in a bone of the patient's foot. For example, in some embodiments, the bone graft composition is configured to be disposed in an opening of a calcaneus (i.e., heel bone) (e.g., bone graft composition 80), navicular (e.g., bone graft composition 82), talus, cuboid, or cuneiform bone of the foot. In another example, referring to FIG. 1H, a bone graft composition can be in the form of an implant 84 configured to be disposed at a target repair site in or proximate to an ankle joint, i.e., between the tibia and the talus.

In some embodiments, referring to FIGS. 2A-2B, the bone graft composition can be in the form of an implant 100 configured for use in or at a target repair site in a patient's cranium to facilitate growth of bone therein. Although specific examples of suitable target repair sites have been illustrated and described, in other embodiments, the bone graft composition can be configured to be implanted into or at a target repair site in a different bone or bony structure of the patient's body.

A bone graft material kit according to an embodiment includes at least a collagen (e.g., a collagen matrix), as described above, and bioactive glass (e.g., in the form of particles), as described above. In some embodiments, the kit includes calcium phosphate, for example in the collagen matrix as described above. The bioactive glass of the kit can be maintained separately within the kit from the collagen. For example, the bioactive glass particles can be disposed in a vial during the manufacturing stage. The vial of bioactive glass particles is packaged with the collagen matrix for delivery to a patient treatment facility. In some embodiments, the bioactive glass particles are included in a solution contained in the vial. The collagen can be separately sealed within the kit. In some embodiments, the collagen matrix is in a second vial, such as when the collagen matrix is in the form of a slurry or foam. In some embodiments, the collagen matrix is sealed within foil or other packaging within the kit, such as when the collagen matrix is in the dried or sponge-like form. In this manner, the bioactive glass can be added by the physician or other healthcare practitioner to the collagen in any suitable manner described herein at a desired time prior to implanting the bone graft material at the target repair site.

Figure 10:
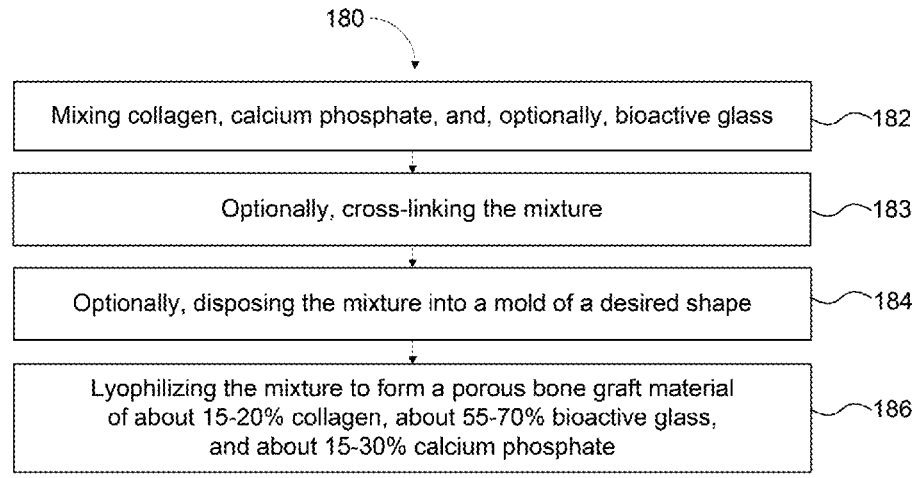
FIG. 10 is a flow chart of a method of making a bone graft material according to an embodiment.

A method 180 of making a bone graft material according to an embodiment is described herein with reference to the flowchart in FIG. 10. The bone graft material can include, for example, any bone graft composition described herein.

In some embodiments, the method optionally includes preparing collagen for inclusion in the bone graft material. The collagen can include any collagen described herein, or combination thereof. The preparing can include preparing the collagen to be a matrix or carrier configured to be implanted at a target repair site and to deliver other components (e.g., an osteoconductive agent, an osteoinductive agent, bioactive glass, calcium phosphate, etc.) to the target repair site. In some embodiments, the preparing the collagen includes preparing collagen that includes type I collagen and type III collagen. In a specific example, the prepared collagen can be collagen a mixture of type I collagen and type III collagen derived from limed bovine corneum where half of the collagen mixture is base processed and half of the collagen mixture is acid swollen gel. In one embodiment, the preparing collagen includes chilling a desired amount of type I collagen at about 2° to about 10° C. For example, the preparation of type I collagen can be chilled until the type I collagen weighs about 100 mL at equilibrium. The preparing collagen includes weighing out a desired amount of type III collagen. For example, an about 1 gram preparation of type III collagen can be weighed out. The preparing collagen further includes mixing the type III collagen with the type I collagen. The mixture of type III collagen and type I collagen can optionally be stored (e.g., overnight) at about 2° to about 10° C. Although the prepared collagen is described herein including type I collagen and type III collagen, in other embodiments, the prepared collagen includes type I collagen and a type of collagen different than type I or type III collagen (e.g., type VII collagen).

Optionally, a phosphate solution is added to the mixture of type III collagen and type I collagen. For example, 0.2 M phosphate with about 0.13 M NaCl can be added to the collagen mixture. Specifically, a 10 mL preparation of the phosphate solution can be added to the collagen mixture. Optionally, the collagen mixture with the added phosphate is titrated. For example, the collagen mixture with the added phosphate solution can be titrated with 1 N NaOH until the pH of the mixture is within the range of about 7.0 to about 7.8. More specifically, the mixture can have a pH of 7.4. Optionally, the titrated mixture is mixed. For example, the titrated mixture can be mixed for about one minute. Optionally the mixture is held for a desired period of time at a desired temperature with no agitation. For example, the mixture can be left at rest for at least 10 hours at about 2 to about 10° C. with no agitation.

In some embodiments, the method optionally includes weighing out at least one component to be included in the bone graft material. For example, a desired dry weight of at least one component (e.g., the calcium phosphate and/or the bioactive glass) can be weighted out. In another example, in some embodiments, the collagen is in a flowable form (such as a slurry of collagen and water). As such, a desired dry weight of collagen is calculated based on the concentration, e.g., of the slurry, and is weighed out volumetrically. For example, to obtain 2 grams of collagen from a slurry having a concentration of 20 mg of collagen per 1 mL of liquid, a 100 mL collagen slurry is volumetrically weighed out. In one embodiment for making a bone graft material including collagen, calcium phosphate, and bioactive glass, the method includes weighing out a desired amount of at least one of the collagen, the calcium phosphate, and the bioactive glass. In yet another example, an embodiment for making a bone graft material including collagen and bioactive glass can include weighing out a desired amount of at least one of the collagen and the bioactive glass.

At step 182, the method 180 includes mixing collagen with calcium phosphate. For example, the mixing can include mixing the weighed out amounts of collagen and calcium phosphate. In some embodiments, the mixing includes mixing the collagen into a slurry or foam. The mixing at step 182 can include pouring the calcium phosphate (e.g., in the form of granules) into the collagen. The calcium phosphate is mixed with the collagen (e.g., using a spatula or other apparatus for hand-mixing the components). The collagen and calcium phosphate can optionally be mixed until the mixture is substantially homogenous (e.g., until the mixture visually appears to be homogenous).

Optionally, the mixing at step 182 includes mixing bioactive glass with the collagen and calcium phosphate. For example, a weighed out amount of bioactive glass particles can be poured into and mixed with the collagen in a similar manner as described above with respect to mixing the calcium phosphate with the collagen. The bioactive glass and calcium phosphate can be added to and mixed with the collagen consecutively (with either of the bioactive glass and the calcium phosphate being added before the other of the bioactive glass and the calcium phosphate) or concurrently. The mixture of collagen and calcium phosphate, and optionally bioactive glass, is referred to herein with respect to method 180 as the collagen mixture.

At step 183, the method 180 optionally includes cross-linking the collagen mixture. More specifically, cross-linking the collagen mixture includes cross-linking the collagen (e.g., by forming a bond between collagen fibrils). In some embodiments, the cross-linking includes preparing a solution of glutaraldehyde and phosphate buffer. For example, in some embodiments, a solution of 25% glutaraldehyde solution and 0.02 M phosphate buffer is prepared. Specifically, for example, a solution of 50 μL of the 25% glutaraldehyde solution and 100 mL 0.02 M phosphate buffer with a pH of 7.4 is prepared. The collagen mixture is placed into the solution for a desired length of time for cross-linking to occur. For example, in some embodiments, the collagen mixture is placed into the solution and is cross-linked for about thirty minutes at room temperature. The cross-linked collagen mixture is removed from the solution.

Figure 3:
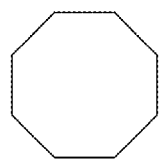
FIGS. 3-6 are top views of bone graft materials according to embodiments.
Figure 4:
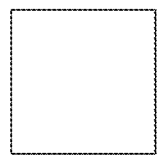
Figure 5:
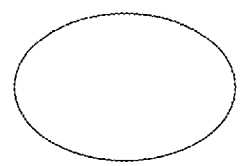
Figure 6:
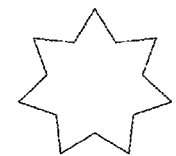
Figure 7:
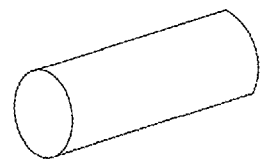
FIGS. 7-9 are perspective views of bone graft materials according to embodiments.
Figure 8:
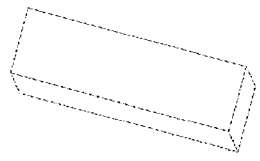
Figure 9:

At step 184, the method 180 optionally includes disposing the collagen mixture into at least one mold having a desired shape. The disposing can include scooping or pouring the collagen mixture into the mold. The collagen mixture can be molded into any desired shape for repair of bone at a target repair site. For example, the mold can have a shape that mimics or correlates to the shape of the target repair site. In another example, the collagen mixture can be molded into the shape of a circle (e.g., FIG. 2A), polygon (e.g., FIG. 3), square (e.g., FIG. 4), oval (e.g., FIG. 5), star (e.g., FIG. 6), cone, cylinder (e.g., FIG. 7), rectangle (e.g., FIG. 8), cube, disk, dowel, plug (e.g., FIG. 9), or other suitable shape. More specifically, in some embodiments, the collagen mixture is molded into a three-dimensional rectangular shaped implant that has a length about three times greater than a width of the implant. In some embodiments, the collagen mixture is molded into an implant that has a width up to about four times a depth of the implant. For example, the collagen mixture can be molded into an implant that is about 50 mm in length, 15 mm in width, and 4 mm in depth. The disposing the collagen mixture into a mold can include disposing the mixture into the mold while the mixture is in a flowable form (e.g., in the form of a slurry or foam).

At step 186, the method 180 includes lyophilizing the collagen mixture to form a porous bone graft material. In some embodiments, the method 180 results in the bone graft material being about 15% to about 20% by weight collagen, about 55% to about 70% by weight bioactive glass, and about 15% to about 30% by weight calcium phosphate. The bioactive glass and the calcium phosphate together can be about 80% to about 85% by weight of the resulting bone graft material. When the bone graft material is lyophilized, the collagen can form a hardened, brittle, or otherwise dry cracker-like material. In some embodiments, the porous bone graft material has about 70% porosity. The bone graft material is neither compressive molded nor annealed.

In some embodiments, the method optionally includes wetting (i.e., hydrating) the bone graft material. For example, the lyophilized bone graft material can be wetted with a suitable solution, as described above. In some embodiments, the wetting includes wetting the bone graft material with a suitable solution that includes bioactive glass particles. In some embodiments, the method optionally includes disposing bioactive glass particles onto the wetted bone graft material, for example by sprinkling the bioactive glass particles onto a surface of the wetted bone graft material. Upon wetting (or re-wetting), at least a portion of the bone graft material (e.g., the collagen body portion) can be flexible and/or moldable.

The method optionally includes packaging the porous bone graft material. For example, the bone graft material can be placed in a foil wrapper and sealed therein.

The method optionally includes irradiating the porous bone graft material. The irradiating can help kill any bacteria or other contaminants that may be present in or on the bone graft material. The bone graft material can be irradiated at any appropriate level for sterilizing the bone graft material. For example, the bone graft material can be gamma irradiated at about 25-40 kGy. In some embodiments, the bone graft material is irradiated after the packaging of the material. Irradiation of the bone graft material in the foil packaging, for example, can help ensure the bone graft material remains sterile during shipment of the bone graft material from the manufacturer to a patient treatment facility.

A bone graft procedure according to an embodiment includes a method for implanting a bone graft material or composition (including any bone graft material or composition described herein) at a target repair site within a body of a patient. The bone graft procedure optionally includes preparing the target repair site of the bone or bony structure within the patient's body to receive the bone graft material. Preparation of the target repair site can include cleansing the site to remove foreign materials, loose bone fragments or powder, or other potentially harmful materials. In some procedures, preparation of the target repair site includes re-shaping the site, for example, by removing a portion of the perimeter of the site so that the site has a desired shape.

The bone graft procedure includes selecting a bone graft material. For example, in some embodiments, a physician or other healthcare provider can select a bone graft material having a shape corresponding to a shape of the target repair site. In other embodiments, a physician can select a flowable or moldable bone graft material. For example, the physician can select a bone graft material configured to be manually molded (e.g., by the physician).

The bone graft procedure optionally includes shaping the bone graft material for placement at the target repair site. For example, the physician can manually manipulate (e.g., squeeze, pinch, stretch, etc.) the bone graft material (e.g., when the bone graft material is in the sponge-like form). In another example, the physician can pour a flowable bone graft material into a mold and dry the material so that the material retains the shape of the mold, in a similar manner as described with respect to the method 180 of making a bone graft material above. In some embodiments, shaping the bone graft material includes cutting the bone graft material into a desired shape.

The bone graft procedure optionally includes wetting the bone graft material with a suitable solution. In some embodiments, the suitable solution includes bioactive glass particles. In some embodiments, bioactive glass particles are disposed on the bone graft material after the material is wetted with the suitable solution.

The bone graft procedure includes positioning the bone graft material at the target repair site. In some embodiments, positioning the bone graft material includes injecting the bone graft material in a flowable state into the target repair site. For example, the bone graft material can be in the form of a slurry, foam, paste, solution, or the like, which is injected into the target repair site via a syringe. In some embodiments, positioning the bone graft material includes placing a bone graft material in a dried or sponge-like form into the target repair site. For example, a dried or sponge-like bone graft material having a shape corresponding to the shape of the target repair site can be positioned so that the shape of the bone graft material is aligned with the shape of the target repair site. In this manner, the material is suitable for the repair of substantially any shaped target repair site.

Optionally, at the physician's discretion, the bone graft procedure includes wetting the bone graft material with a suitable solution after positioning the bone graft material at the target repair site. In some embodiments, the bone graft material is wetted with a fluid from the patient's body. For example, blood or plasma from the patient's body can be disposed on or permitted to flow to the bone graft material.

The bone graft procedure optionally includes closing an aperture in the patient's body that provided access to the target repair site. For example, a skin flap can be repositioned over the implanted bone graft material. In some embodiments, sutures, staples, or another closure mechanism are used to help close the aperture in the patient's body. The patient can be monitored for symptoms of complication (e.g., infection, rejection of the bone graft material), as well as for regrowth of bone at the target repair site.

While various embodiments have been described herein, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. For example, in some embodiments, the collagen mixture can be cross-linked after being disposed in the mold. In another example, in some embodiments, the collagen mixture can be lyophilized before, or both before and after being cross-linked. In another example, in some embodiments, the material is irradiated prior to packaging the material. Furthermore, each activity is not required for making the bone graft material. For example, in some embodiments, a collagen need not be prepared as described prior to mixing the collagen with calcium phosphate. Additionally, certain of the steps may be performed concurrently in a parallel process when possible, as well as performed sequentially as described above. The embodiments have been particularly shown and described, but it will be understood that various changes in form and details may be made.

For example, although the method for making a bone graft material includes lyophilizing the mixture of collagen and calcium phosphate (and, optionally, bioactive glass), in other embodiments, a mixture can be dried in a different manner. For example, in some embodiments, a mixture of collagen and calcium phosphate (and, optionally, bioactive glass) can be heat dried. A dry-heat process can also be configured to concurrently sterilize the mixture.

Although the bone graft compositions (or materials) have been described herein as being in a certain form (e.g., flowable, dried, sponge-like), in some embodiments, a bone graft composition can have a first configuration in which the composition is in a first form and a second configuration in which the composition is in a second form different than the first form. For example, in some embodiments, a bone graft composition includes a collagen matrix in a first form (e.g., a dried form) for delivery from the manufacturing facility to the patient treatment facility, and in a second form (e.g., the sponge-like form) for implantation at the target repair site of the patient's body.

Specific examples of bone graft compositions according to embodiments are now described, with reference to the following cell preparation and sample preparation procedures.

EXAMPLE 1

Cell Preparation

Osteoblast-like MG-63 cells were prepared per American Type Culture Collection ("ATCC") instructions. From passage three, the MG63 cells were stored frozen at −70° C. in Eagle's minimum essential medium ("EMEM") with 20% fetal bovine serum ("FBS"). In preparation for use, the MG63 cells were thawed and then grown for at least three passages using EMEM. After three passages, the cells were transferred to Dulbecco's modified EMEM ("DMEM"). The DMEM contained no glucose and was supplemented with ascorbic acid (50 µg/mL), 10 mM β-glycerophosphate, 50 UI/mL Penicillin-Streptomycin and 10% FBS. The cells were grown for at least three more passages at these conditions. The cells were maintained at 37±1° C. in a humidified incubator with 5±1% $CO_2$. The media was changed every 2 to 3 days. After the cells became confluent on the last passage, they were harvested and counted.

EXAMPLE 2

Sample Preparation

Test samples of bone graft compositions including collagen, bioactive glass, and calcium phosphate (60% HA/40% TCP) and test samples of bone graft compositions including collagen and bioactive glass were prepared. The following preparation and testing was performed for each bone graft composition test sample. Each compound (i.e., collagen, bioactive glass, and calcium phosphate, as applicable; ratios of compounds each test sample are described below in Examples 3 through 8) was weighed aseptically using an analytical scale under a biological safety cabinet and transferred to a sterile non-treated tissue culture Petri dish (60×15 mm). A 30 mg mixture of the compounds in the specified ratio was aseptically prepared. The 30 mg mixture was transferred to and divided amongst four Petri dishes, each non-treated. A 1 mL PBS was added to each dish. Each dish was then vigorously swirled by hand on a desk surface. Each dish was also spun in a centrifuge at 3000 rpm for 5 minutes for even distribution of the composition on the dishes and to stick the compounds to the dishes.

Osteoblast-like MG-63 cells prepared according to Example 1 were re-suspended in media with supplements to a seeding concentration of approximately $2\times10^4$ cell/cm$^2$. Next, 5 mL of the cells with media was carefully added to each of the four dishes with the bone graft compositions. The dishes were each gently swirled to spread the composition and cells. The cells were incubated in the dishes at $37\pm1°$ C. in a humidified incubator with $5\pm1\%$ $CO_2$.

A control with collagen and calcium phosphate, but no bioactive glass, was prepared according to the foregoing steps. The control included a mixture of 10 mg collagen and 20 mg calcium phosphate. The 30 mg collagen and calcium phosphate mixture was transferred to and divided amongst four Petri dishes. Cells were added to each of the four dishes in the same manner described above.

Cells were observed daily for 11 days. The media was changed carefully every 3 days. Cell confluence was observed and recorded at days 5 and 11. The percentage of cell confluence indicated a percentage coverage of the bottom of the Petri dish by the cultured cells at different phases of growth. As used herein, aggregation refers to cells composed of dense clusters of separate units and splicing of cells. Any differences (e.g., no cell growth, loose cells, and change in cell appearance) between the samples, the cell culture control, and the collagen-calcium phosphate control were recorded and pictures were taken of representative plates.

On day 11, methanol was added to fix the cells. The cells were stained directly in the dishes using 3 staining methods: Calcium Stain Kit (modified Van Kossa staining), Trichrome staining (modified Masson's staining), and H&E (Hemotoxylin & Eosin) staining. The staining methods aided in differentiating cells and their metabolites, if present. The different staining methods also aided in observing changes in cell morphology in the various bone graft formulations.

Consideration regarding mineralization of each bone graft formulation was based on the Calcium staining. According to the staining kit notes, cells with accumulated dispersed calcium must stain in gray color versus black staining for calcium in mass deposits. Mineralization level, as a percentage, was assumed by calculating a ratio based on the size of the calcium crystals and counting of bioactive glass crystals in multiple fields around the dish surface with gray formations on the surface of crystals and around borders of them (e.g., aureole, fluffy collagen-cellular fringe, etc.) versus crystals which looked intact (e.g., clear borders, no changes). The Trichrome and H&E Staining were performed to more clearly visualize changes of collagen scaffolds and changes in cell appearance and density. Generally, the brighter the color, the higher the density of cells.

EXAMPLE 3

Collagen:Bioactive Glass:Calcium Phosphate (15:65:20)

Figure 11A:
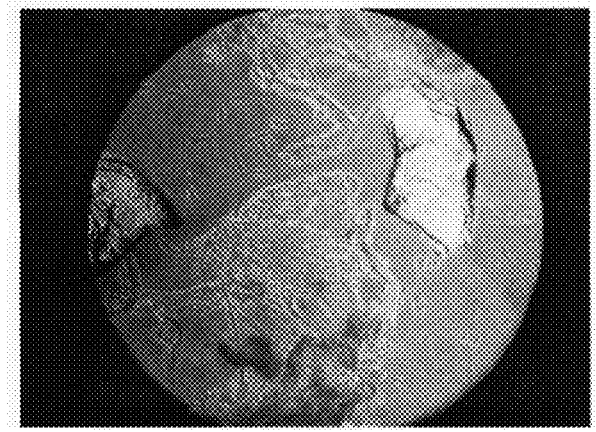
FIGS. 11A-11C are representative images of a sample preparation of a bone graft composition according to Example 3 at day 2, day 7, and day 11, respectively.
Figure 11B:
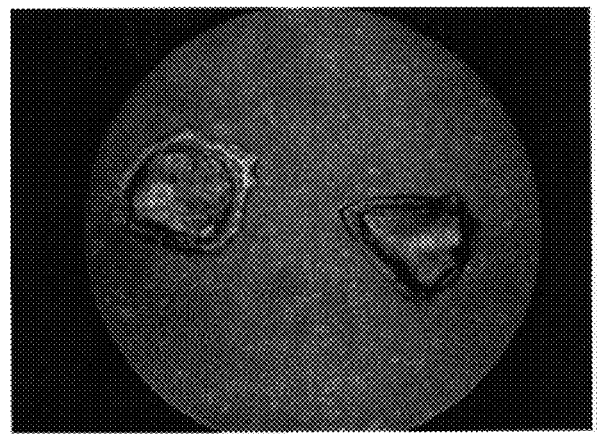
Figure 11C:
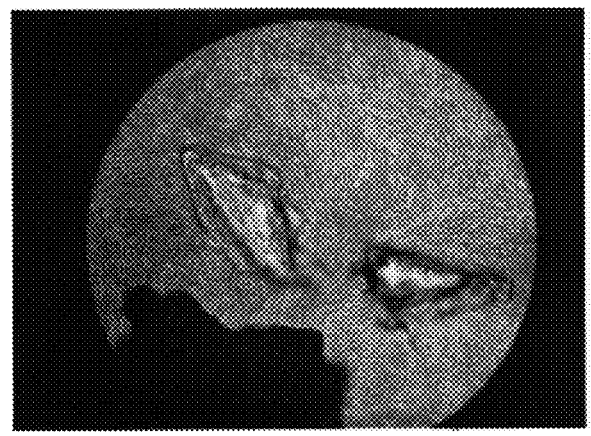
Figure 13:
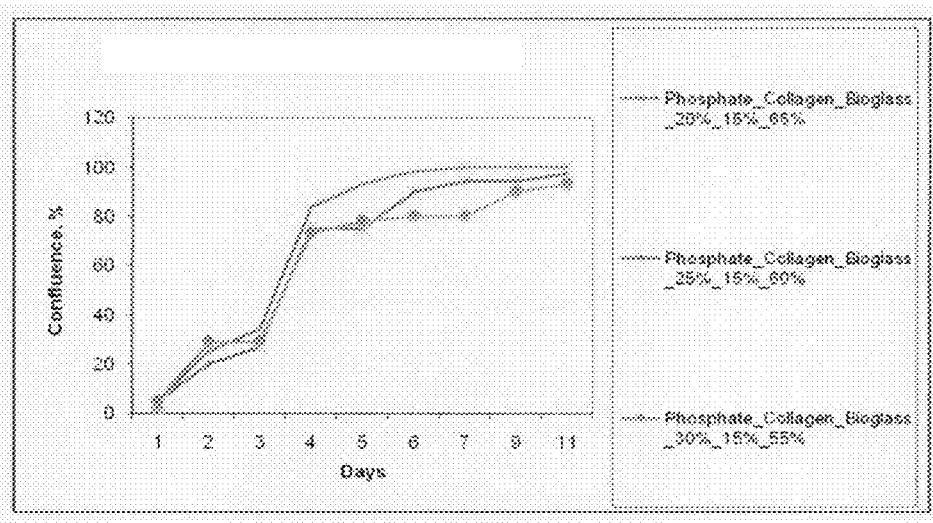
FIG. 13 is a chart comparing cell confluence of sample preparations of bone graft compositions according to Examples 3, 4, and 5.

A test sample of a bone graft composition including 15% collagen, 65% bioactive glass, and 20% calcium phosphate (60% HA/40% TCP) was prepared according to Example 2. Cell confluence was determined based on visual observation of the sample without staining, as shown in the images of the sample taken on day 2, day 5, and day 11 in FIGS. 11A-11C, respectively. Cell confluence reached nearly an average of 93% by day 5. Cell confluence reached about 100% by day 11. No cytotoxicity was observed when compared with cell controls. A chart of cell confluence of this Example 3 compared to Examples 4 and 5 below is shown in FIG. 13.

Figure 12A:
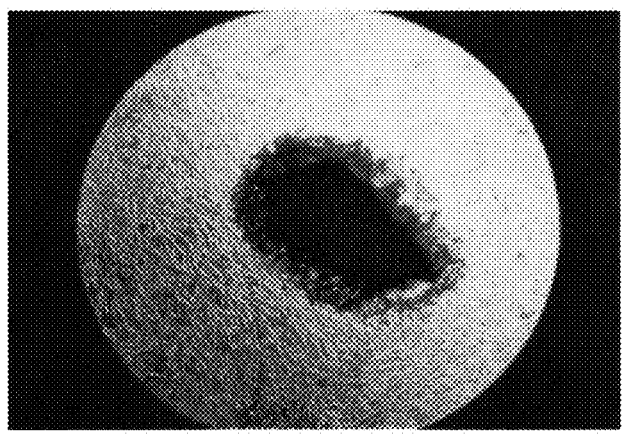
FIGS. 12A-12C are stained representative images of the sample preparation of a bone graft composition according to Example 3 at day 11.
Figure 14:
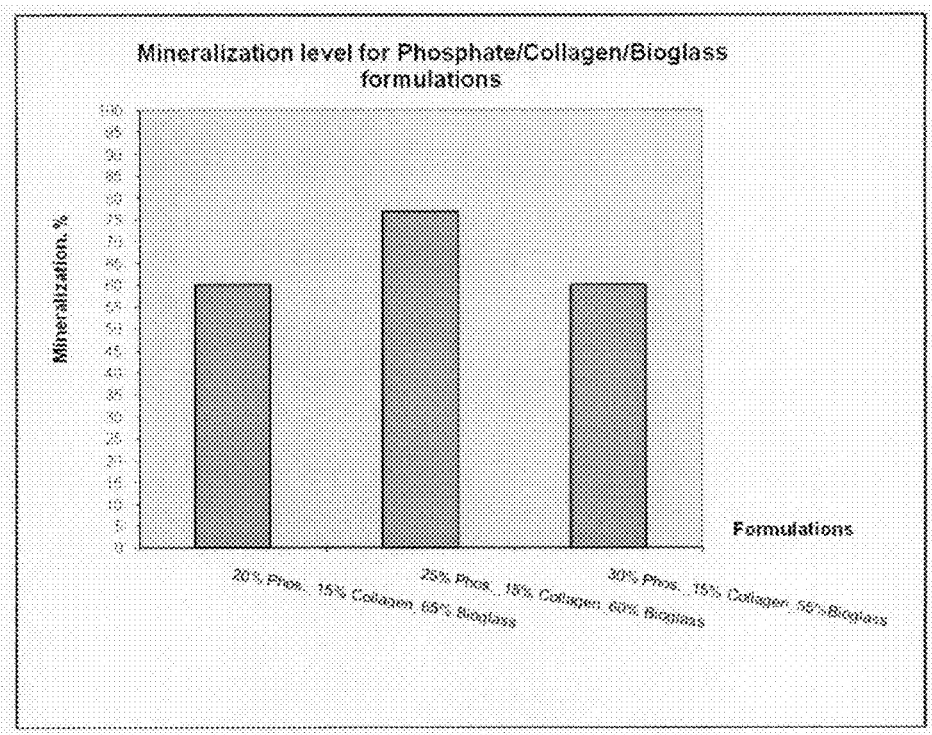
FIG. 14 is a chart comparing mineralization levels of sample preparations of bone graft compositions according to Examples 3, 4, and 5.

Referring to FIG. 12A, visual observation under light microscopy of the Van Kossa stained cells showed pink, large, prolonged cells with dark-red big nuclei. The cells were in a fairly thick multilayer with many aggregations. Some crystals and phosphates appeared intact, but with grayish aureole. Some of the bioactive glass crystals and phosphates had collagen-cellular fringe and appeared very fluffy. This may be due to the presence of dispersed calcium accumulated by the cells. The collagen scaffolds show high cell growth. The composition appeared to achieve approximately 60% bioactive glass mineralization with medium size calcium crystals. A chart of mineralization levels of this Example 3 compared to Examples 4 and 5 below is shown in FIG. 14.

Figure 12B:
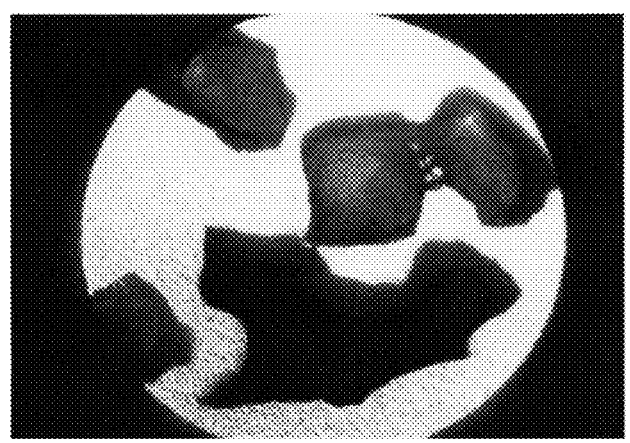

Referring to FIG. 12B, visual observation under light microscopy of the H&E stained cells showed pink-purple cells of regular shape with blue big nuclei. The cells were in a fairly dense multilayer surrounding most of the bone graft composition. Many phosphates and bioactive glass crystals were densely covered by cells or had layers of climbing cells. The collagen scaffolds were rich by cells.

Figure 12C:
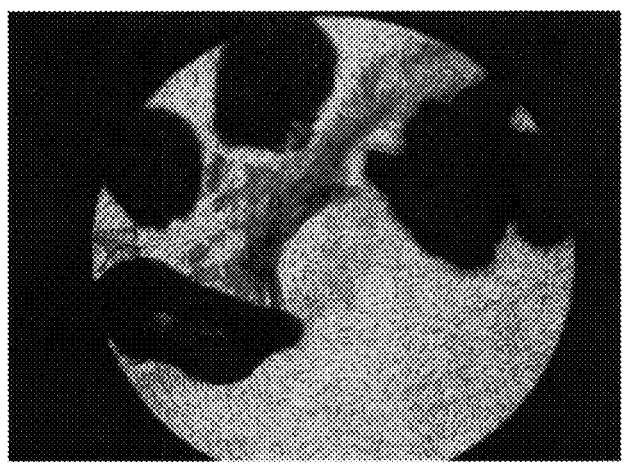

Referring to FIG. 12C, visual observation under light microscopy of the Trichrome stained cells showed bright red cells of regular shape. The cells were mostly in a dense multilayer, especially around different scaffolds (collagen, bioactive glass crystals, calcium phosphates), with some aggregations. Many (about 90%-95%) bioactive glass crystals and calcium phosphates were densely covered by cells, some with layers of climbing cells or collagen-cellular fringe. Few bioactive glass crystals appeared intact.

EXAMPLE 4

Collagen:Bioactive Glass:Calcium Phosphate (15:60:25)

Figure 15A:
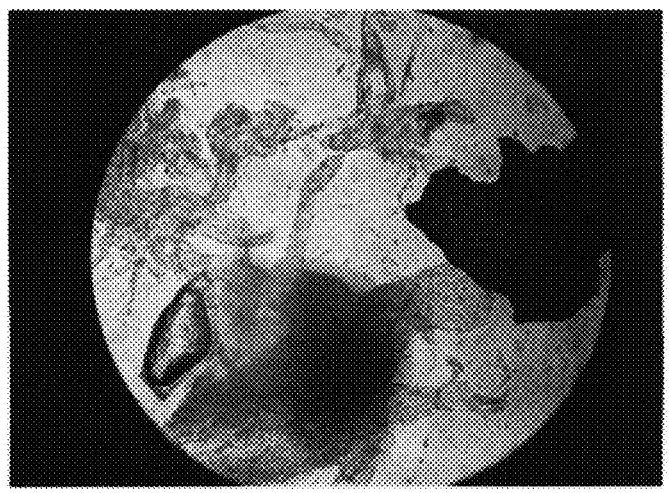
FIGS. 15A-15C are representative images of a sample preparation of a bone graft composition according to Example 4 at day 2, day 7, and day 11, respectively.
Figure 15B:
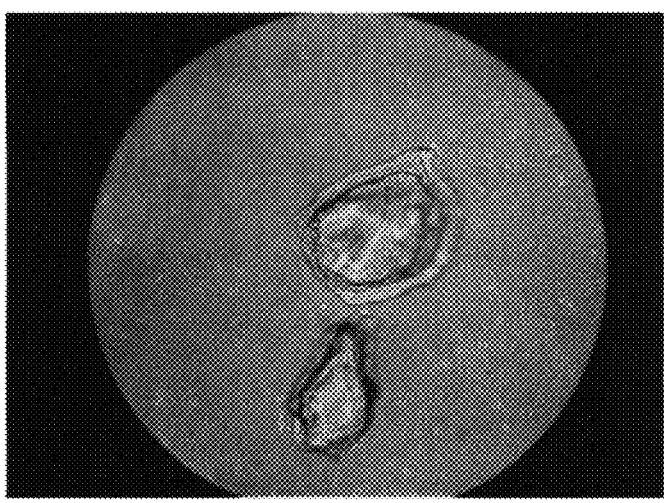
Figure 15C:
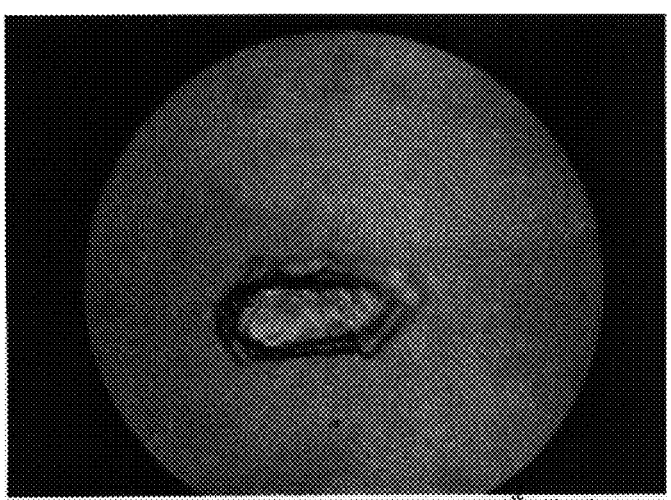

A test sample of a bone graft composition including 15% collagen, 60% bioactive glass, and 25% calcium phosphate (60% HA/40% TCP) was prepared according to Example 2. Cell confluence was determined based on visual observation of the sample without staining, as shown in the images of the sample taken on day 2, day 5, and day 11 in FIGS. 15A-15C, respectively. Cell confluence reached nearly 75% by day 5. Cell confluence reached about 97% in average at the end by day 11. No cytotoxicity was observed when compared with cell controls. A chart of cell confluence of this Example 4 compared to Examples 3 and 5 (below) is shown in FIG. 13.

Figure 16A:
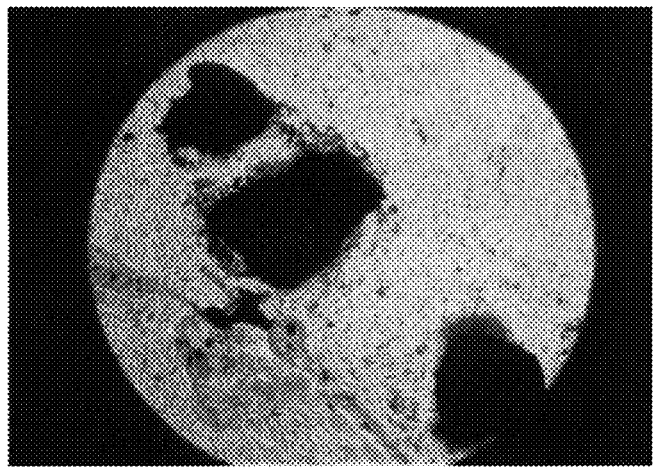
FIGS. 16A-16C are stained representative images of the sample preparation of a bone graft composition according to Example 4 at day 11.

Referring to FIG. 16A, visual observation under light microscopy of the Van Kossa stained cells showed pink, large prolonged regular shaped cells with big red nuclei. Cell growth was uneven, with some areas having a monolayer or poor growth. Many crystals and phosphates had layers of climbing cells or were densely covered by cells. Many crystals appeared fluffy. Many crystals were covered by grayish collagen-cellular fringe, which appeared to be dispersed calcium that could be considered in the cells. Some crystal had clear borders surrounded by grayish aureole. The composition appeared to achieve approximately 77% bioactive glass mineralization with large calcium crystals. A chart of mineralization levels of this Example 4 compared to Examples 3 and 5 (below) is shown in FIG. 14.

Figure 16B:
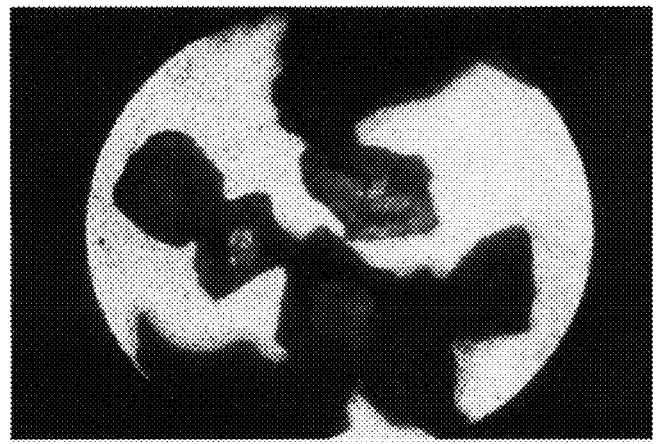

Referring to FIG. 16B, visual observation under light microscopy of the H&E stained cells showed purple-pink, large, regular shaped cells with blue big nuclei. The cells were mostly in thick, dense multilayer. Some areas showed a thin layer of cells. Much of the bone graft composition was covered by a dense net of cells.

Figure 16C:
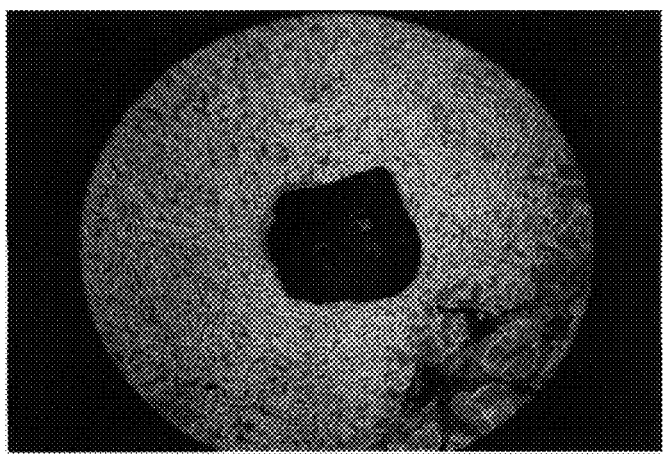

Referring to FIG. 16C, visual observation under light microscopy of the Trichrome stained cells showed red, normal cells in a very dense multilayer. Some phosphates granules were surrounded by a very thin layer of cells, especially on the borders of the dishes. Most (about 95%) of the bone graft composition was densely covered by cells.

EXAMPLE 5

Collagen:Bioactive Glass:Calcium Phosphate (15:55:30)

Figure 17A:
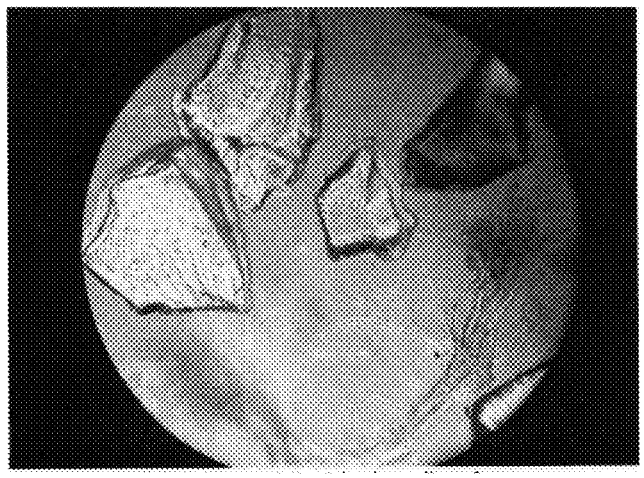
FIGS. 17A-17C are representative images of a sample preparation of a bone graft composition according to Example 5 at day 2, day 7, and day 11, respectively.
Figure 17B:
Figure 17C:

A test sample of a bone graft composition including 15% collagen, 55% bioactive glass, and 30% calcium phosphate (60% HA/40% TCP) was prepared according to Example 2. Cell confluence was determined based on visual observation of the sample without staining, as shown in the images of the sample taken on day 2, day 5, and day 11 in FIGS. 17A-17C, respectively. Cell confluence reached nearly 80% by day 5. Cell confluence reached about 93% by day 11. No cytotoxicity was observed when compared with cell controls. A chart of cell confluence of this Example 5 compared to Examples 3 and 4 above is shown in FIG. 13.

Figure 18A:
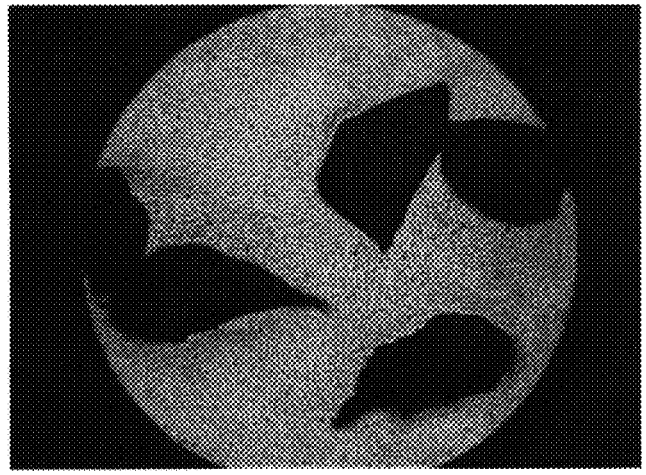
FIGS. 18A-18C are stained representative images of the sample preparation of a bone graft composition according to Example 3 at day 11.

Referring to FIG. 18A, visual observation under light microscopy of the Van Kossa stained cells showed large prolonged regular shaped cells with big nuclei in fairly thick high density multilayer especially around the bone graft composition. Many phosphate granules and bioactive glass crystals were observed to have grayish aureole and fuzzy borders, some with layers of climbing cells. Some of the bioactive glass crystals have collagen-cellular fringe on the surface and appear fluffy and grayish. This appeared to be due to the presence of dispersed calcium accumulated by cells, as other bioactive glass crystals have mostly clear borders and appear intact. The composition appeared to achieve approximately 60% bioactive glass mineralization with medium size crystals. A chart of mineralization levels of this Example 5 compared to Examples 3 and 4 above is shown in FIG. 14.

Figure 18B:
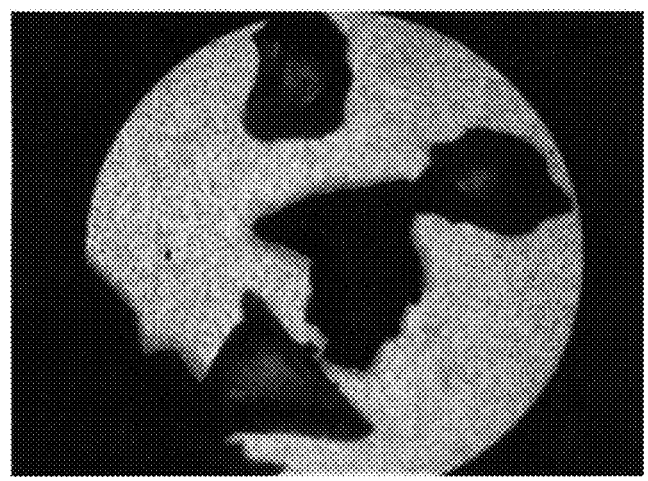

Referring to FIG. 18B, visual observation under light microscopy of the H&E stained cells showed that the cells appeared healthy and regular in shape with large nuclei. The cells were mostly in fairly thick, high-density multilayer with some aggregations. Many crystals were covered by the cells net, some with attached collagen fringe with high cells growth. Many crystals and phosphate had layers of climbing cells on the edges.

Figure 18C:
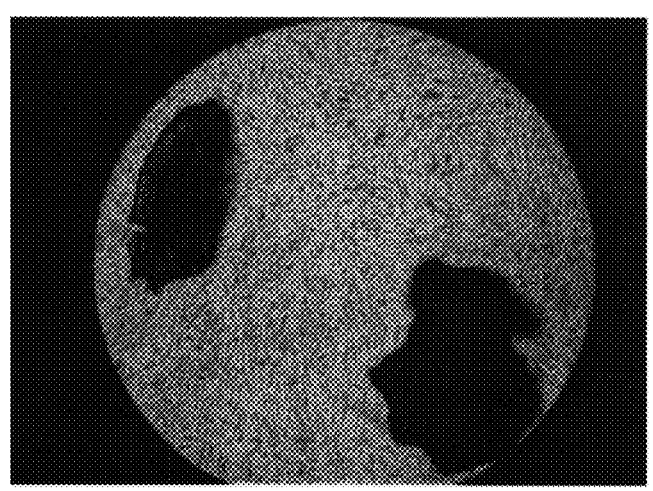

Referring to FIG. 18C, visual observation under light microscopy of the Trichrome stained cells showed many phosphate granules and bioactive glass crystals were covered by a net of dense cells. The cells appeared normal and of regular shape in a thick multilayer. Some crystals had cellular-collagen fringe. The collagen scaffolds had high cell growth, but some of the bone graft composition remained intact.

Each of the bone graft compositions in Examples 3, 4, and 5 promoted good cell proliferation and had good cytocompatibility. Cells appeared healthy, mostly in multilayer of different density depending on the composition. Cells were large, prolonged or star-like, and regularly shaped with big nuclei, which is typical growth for osteoblast cells.

EXAMPLE 6

Collagen:Bioactive Glass (20:80)

Figure 19:
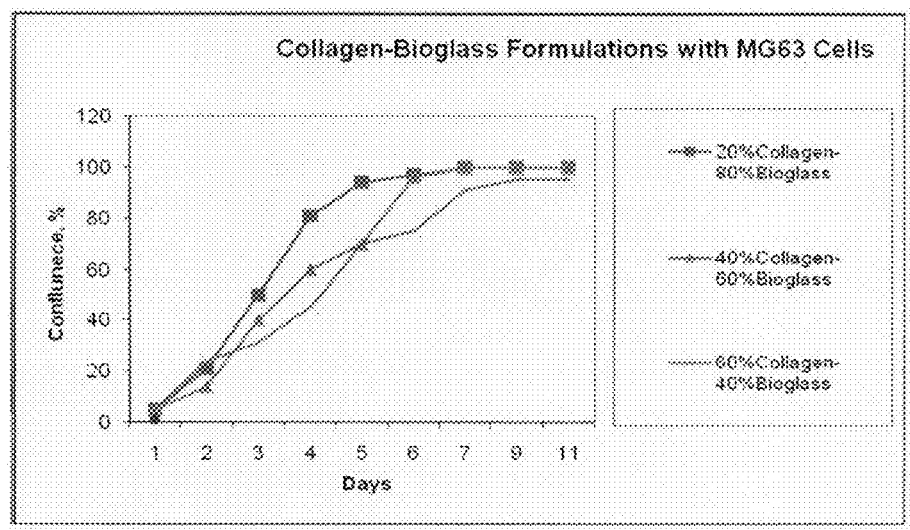
FIG. 19 is a chart comparing cell confluence of sample preparations of bone graft compositions according to Examples 6, 7, and 8.
Figure 21A:
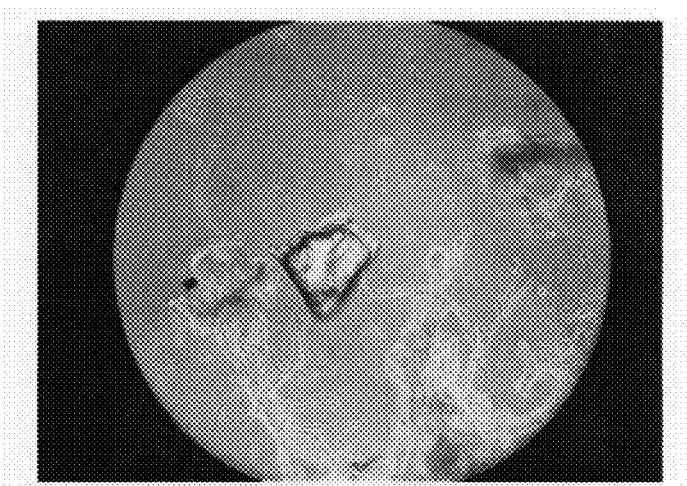
FIGS. 21A-21C are representative images of a sample preparation of a bone graft composition according to Example 6 at day 2, day 7, and day 11, respectively.
Figure 21B:
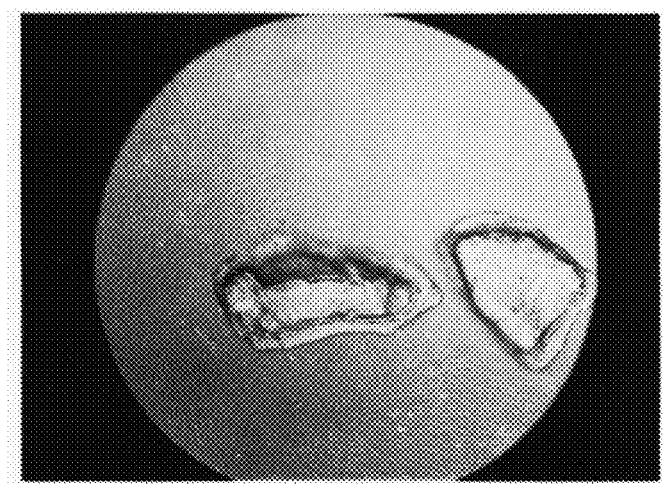
Figure 21C:
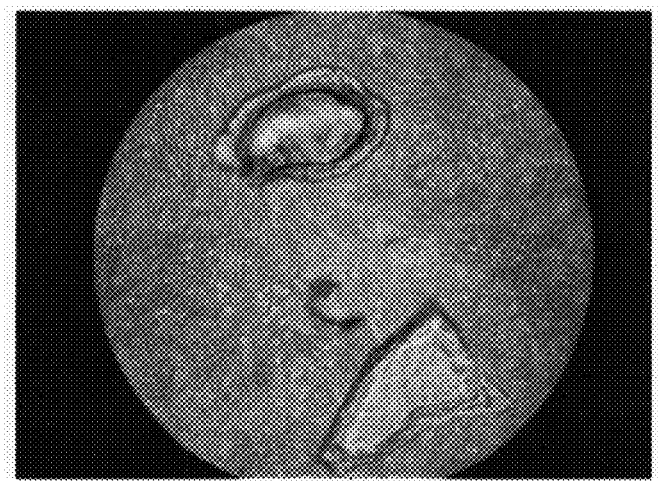

A test sample of a bone graft composition including 20% collagen and 80% bioactive glass was prepared according to Example 2. Cell confluence was determined based on visual observation of the sample without staining, as shown in the images in FIGS. 21A-21C of the sample taken on day 2, day 5, and day 11, respectively. Cell confluence reached 90% by day 5. Cell confluence reached 100% by day 11. No cytotoxicity was observed when compared with cell controls. A chart of cell confluence of this Example 6 compared to Examples 7 and 8 below is shown in FIG. 19.

Figure 20:
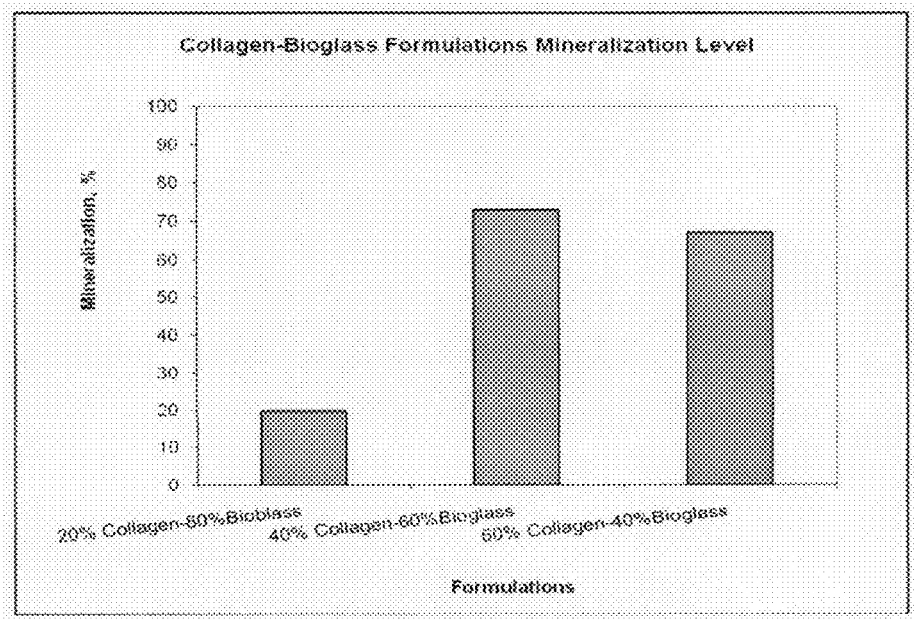
FIG. 20 is a chart comparing mineralization levels of sample preparations of bone graft compositions according to Examples 6, 7, and 8.
Figure 22A:
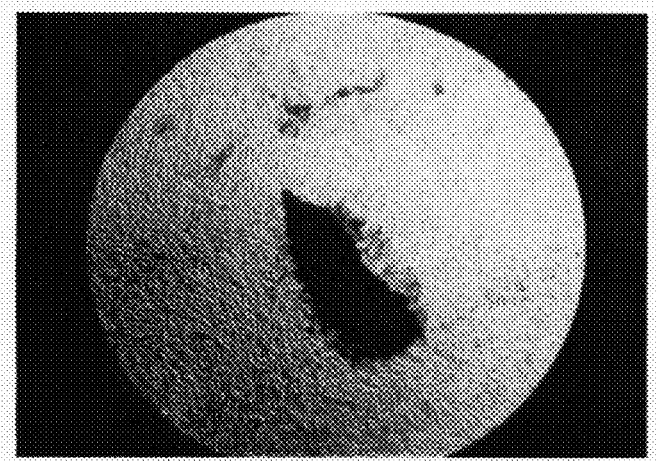
FIGS. 22A-22C are stained representative images of the sample preparation of a bone graft composition according to Example 6 at day 11.

Referring to FIG. 22A, visual observation under light microscopy of the Van Kossa stained cells showed prolonged cells with pink cytoplasm and large red nuclei. Also observed were black bioactive glass crystals. Many crystals showed grayish fuzzy borders, some with fluffy aureole, which appeared to be high cell density with dispersed calcium. The composition appeared to achieve approximately 20% bioactive glass mineralization. A chart of mineralization levels of this Example 6 compared to Examples 7 and 8 below is shown in FIG. 20.

Figure 22B:
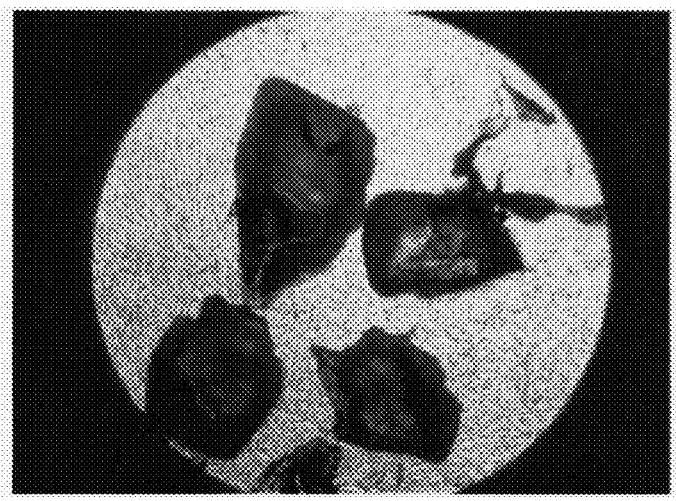

Referring to FIG. 22B, visual observation under light microscopy of the H&E stained cells showed regular shaped, purple-pink cells with large nuclei. Also observed were many crystals with cells on their surface. Most of the crystals appeared intact.

Figure 22C:

Referring to FIG. 22C, visual observation under light microscopy of the Trichrome stained cells showed bright red, regular cells with black-blue large nuclei in a thick multilayer. Many crystals were observed with attached collagen with high cell growth, and with aureole or bright red collagen because of cells growing through. Some crystals were without cells and were intact. Also observed were some chunks of dark-blue collagen.

EXAMPLE 7

Collagen:Bioactive Glass (40:60)

Figure 23A:
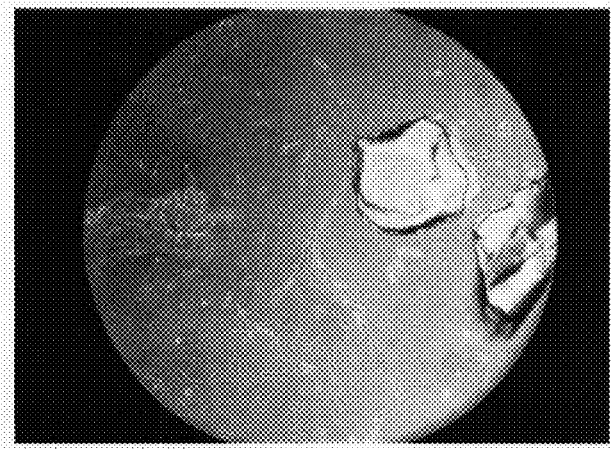
FIGS. 23A-23C are representative images of a sample preparation of a bone graft composition according to Example 7 at day 2, day 7, and day 11, respectively.
Figure 23B:
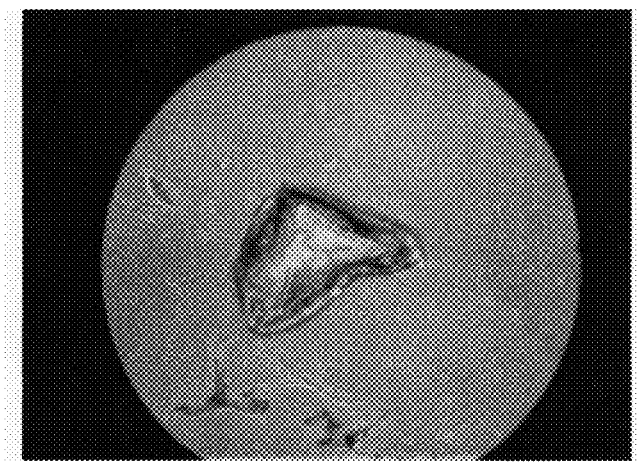
Figure 23C:
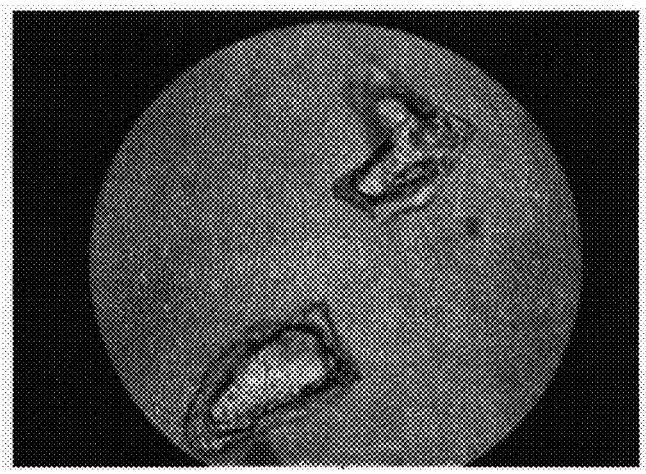

A test sample of a bone graft composition including 40% collagen and 60% bioactive glass was prepared according to Example 2. Cell confluence was determined based on visual observation of the sample without staining, as shown in the images in FIGS. 23A-23C of the sample taken on day 2, day 5, and day 11, respectively. Cell confluence reached 90% by day 5. Cell confluence reached 100% by day 11. No cytotoxicity was observed when compared with cell controls. A chart of cell confluence of this Example 7 compared to Examples 6 and 8 (below) is shown in FIG. 19.

Figure 24A:
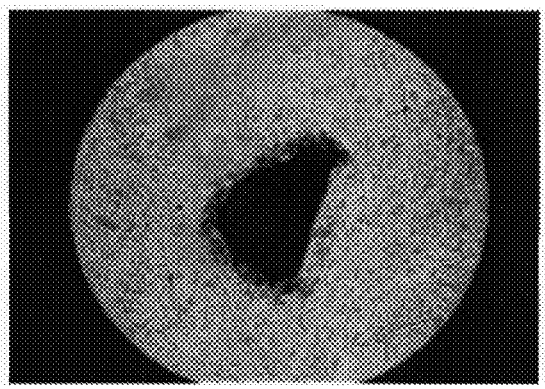
FIGS. 24A-24D are stained representative images of the sample preparation of a bone graft composition according to Example 7 at day 11.

Referring to FIG. 24A, visual observation under light microscopy of the Van Kossa stained cells showed regular shaped pink cells with large red nuclei. Also observed were black bioactive glass crystals. Some crystals showed fuzzy borders and fluffy grayish aureole around the borders, which appeared to be covered by cells with dispersed calcium. The composition appeared to achieve approximately 73% bioactive glass mineralization with large calcium crystals. A chart of mineralization levels of this Example 7 compared to Examples 6 and 8 (below) is shown in FIG. 20.

Figure 24B:
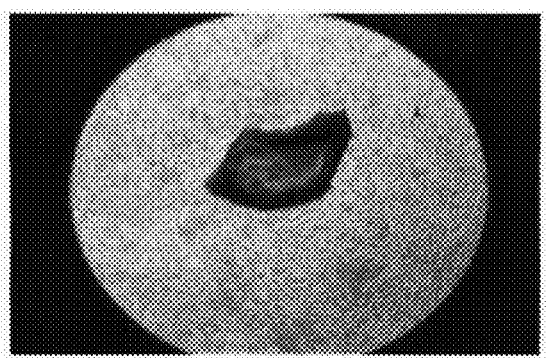

Referring to FIG. 24B, visual observation under light microscopy of the H&E stained cells showed regular shaped, purple-pink cells with large blue nuclei. The bioactive glass crystals appeared to mostly be intact. Some crystals had cells growing on their surface.

Figure 24C:
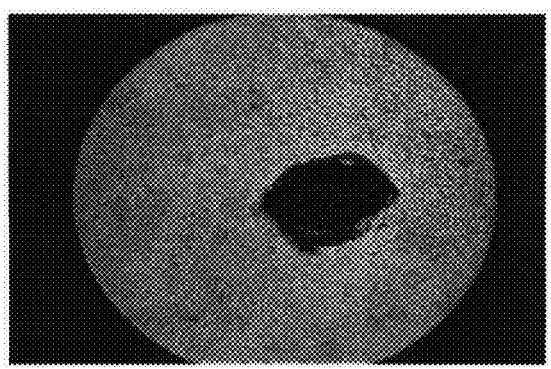
Figure 24D:
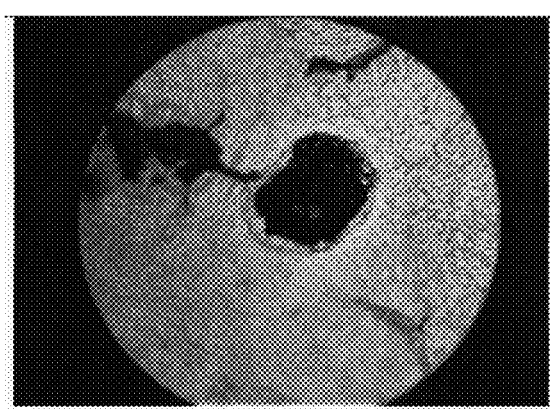

Referring to FIGS. 24C and 24D, visual observation under light microscopy of the Trichrome stained cells showed multilayer of healthy regular shaped cells with large black nuclei. Crystals were mostly intact. Some crystals had attached collagen fringe with high cell growth. Some crystals were covered just by cells without collagen. Structure resembling bone formation was clearly observed.

EXAMPLE 8

Collagen:Bioactive Glass (60:40)

Figure 25A:
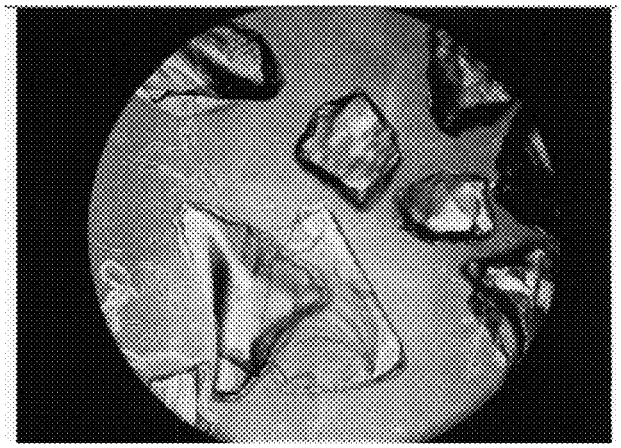
FIGS. 25A-25C are representative images of a sample preparation of a bone graft composition according to an Example 8 at day 2, day 7, and day 11, respectively.
Figure 25B:
Figure 25C:
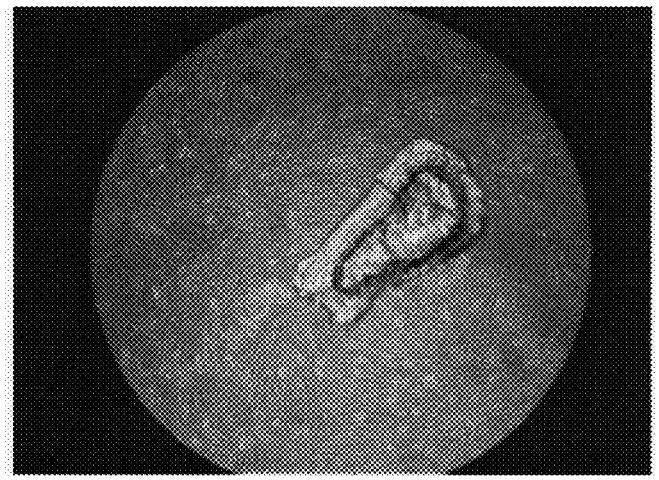

A test sample of a bone graft composition including 60% collagen and 40% bioactive glass was prepared according to Example 2. Cell confluence was determined based on visual observation of the sample without staining, as shown in the images in FIGS. 25A-25C of the sample taken on day 2, day 5, and day 11, respectively. Cell confluence reached 70% by day 5. Cell confluence reached 95% by day 11. No cytotoxicity was observed when compared with cell controls. A chart of cell confluence of this Example 8 compared to Examples 6 and 7 above is shown in FIG. 19.

Figure 26A:
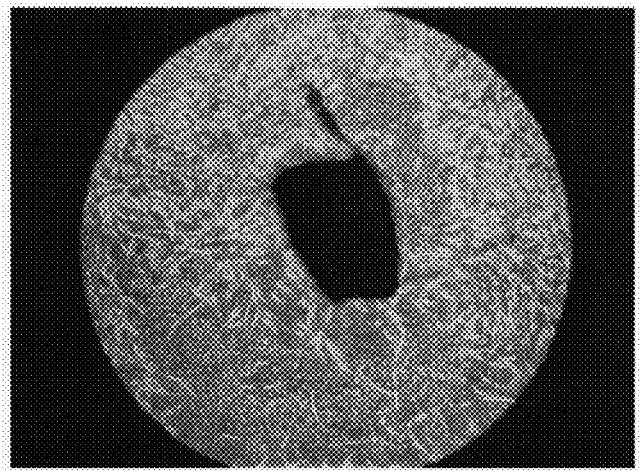
FIGS. 26A-26C are stained representative images of the sample preparation of a bone graft composition according to Example 8 at day 11.

Referring to FIG. 26A, visual observation under light microscopy of the Van Kossa stained cells showed regular shaped pink cells with large red nuclei. Also observed were black bioactive glass crystals, many with stuck collagen fibers. Some crystals had fuzzy borders and fluffy grayish aureole around the borders, which might be covered by cells with dispersed calcium. The composition appeared to achieve approximately 67% bioactive glass mineralization with smaller calcium crystals. A chart of mineralization levels of this Example 8 compared to Examples 6 and 7 above is shown in FIG. 20.

Figure 26B:
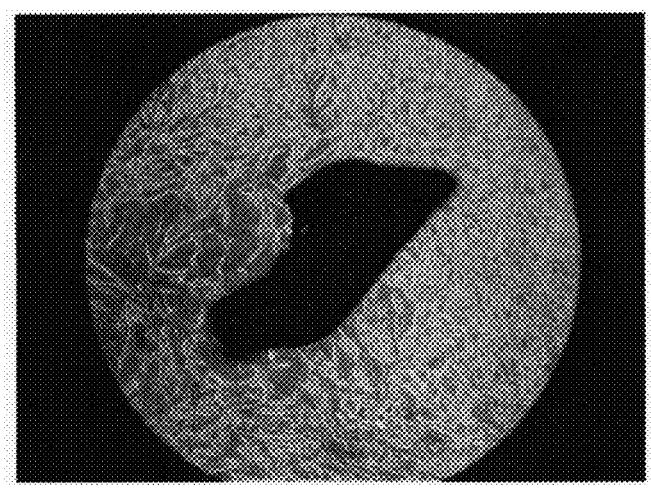

Referring to FIG. 26B, visual observation under light microscopy of the H&E stained cells showed regular shaped, purple-pink cells with large blue nuclei. The crystals appeared mostly intact. Some crystals were observed with cells on their surface.

Figure 26C:
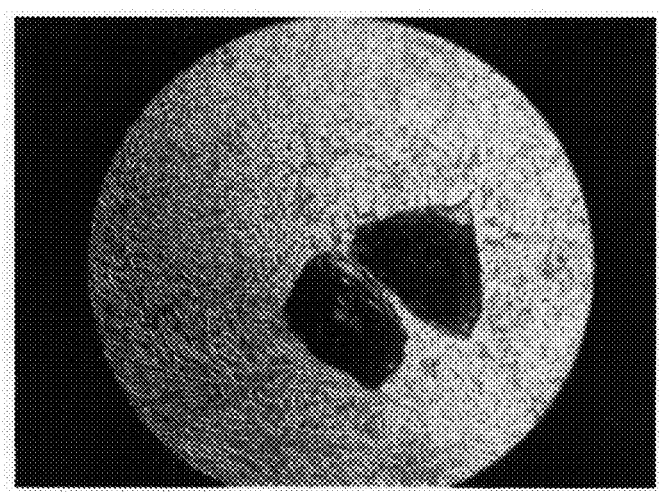

Referring to FIG. 26C, visual observation under light microscopy of the Trichrome stained cells showed multilayer of healthy regular shaped cells with large black nuclei. The crystals were mostly intact. Some crystals had attached collagen fringe with high cell growth. Some crystals were covered just by cells without collagen.

Each of the bone graft compositions in Examples 6, 7, and 8 promoted good cell proliferation, had no cytotoxicity, and had good cytocompatibility. Cells were large, prolonged or star-like, and regularly shaped with big nuclei, which is typical growth for osteoblast cells.

Conclusion

Although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein.

Thus, the breadth and scope of the invention should not be limited by any of the above-described embodiments, but should be defined only in accordance with the following claims and their equivalents. The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

What is claimed is:
1. A bone graft composition comprising:
about 15% to about 20% by weight collagen;
about 55% to about 70% by weight bioactive glass, the bioactive glass having a size within a range of about 53 µm to about 425 µm in size, at least 85% of the bioactive glass having a size within a range of 212 µm to 425 µm in size; and
about 15% to about 30% by weight calcium phosphate.
2. The bone graft composition of claim 1, wherein the bioactive glass and the calcium phosphate together are about 80% to about 85% by weight of the bone graft composition.
3. The bone graft composition of claim 1, wherein the collagen is type I collagen.
4. The bone graft composition of claim 1, wherein the bioactive glass includes particles having a smooth surface.
5. The bone graft composition of claim 1, wherein the calcium phosphate comprises about 40% to about 80% tricalcium phosphate and about 20% to about 60% hydroxyapatite.
6. The bone graft composition of claim 5, further comprising about 15% by weight type I collagen, about 55% to about 65% by weight bioactive glass, and about 20% to about 30% by weight calcium phosphate.
7. The bone graft composition of claim 6, wherein a weight ratio of the collagen to the bioactive glass to the calcium phosphate is about 15%:55%:30%, respectively.
8. The bone graft composition of claim 6, wherein a weight ratio of the collagen to the bioactive glass to the calcium phosphate is about 15%:60%:25%, respectively.
9. The bone graft composition of claim 6, wherein a weight ratio of the collagen to the bioactive glass to the calcium phosphate is about 15%:65%:20%, respectively.
10. The bone graft composition of claim 1, wherein the bioactive glass is 45S5 glass.
11. A bone graft composition consisting of: a collagen and a bioactive glass dispersed throughout the collagen, the bioactive glass having a size within a range of about 53 µm to about 425 µm, at least 85% of the bioactive glass having a size within a range of 212 µm to 425 µm; the collagen and the bioactive glass collectively comprising 100% by weight of the bone graft composition, the collagen being about 20% to about 60% by weight of the bone graft composition and the bioactive glass is about 40% to about 80% by weight of the bone graft composition.

12. The bone graft composition of claim 11, wherein the collagen is in the form of a porous matrix.

13. The bone graft composition of claim 11, wherein the bioactive glass has a smooth surface.

14. The bone graft composition of claim 11, wherein the bioactive glass is about 80% by weight of the bone graft composition.

15. The bone graft composition of claim 11, wherein the bioactive glass is about 60% by weight of the bone graft composition.

16. The bone graft composition of claim 11, wherein the bioactive glass is 45S5 glass.

17. The bone graft composition of claim 11, wherein the collagen includes type I collagen.

* * * * *